US006766190B2

(12) United States Patent
Ferek-Petric

(10) Patent No.: US 6,766,190 B2
(45) Date of Patent: Jul. 20, 2004

(54) METHOD AND APPARATUS FOR DEVELOPING A VECTORCARDIOGRAPH IN AN IMPLANTABLE MEDICAL DEVICE

(75) Inventor: Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 279 days.

(21) Appl. No.: 10/003,547

(22) Filed: Oct. 31, 2001

(65) Prior Publication Data

US 2003/0083587 A1 May 1, 2003

(51) Int. Cl.[7] .................... A61B 5/0402; A61B 5/0452
(52) U.S. Cl. .................... 600/512; 600/509; 607/4
(58) Field of Search .................... 600/509, 512, 600/515–518; 607/9, 14, 25

(56) References Cited

U.S. PATENT DOCUMENTS

| | | | |
|---|---|---|---|
| 4,136,690 A | 1/1979 | Anderson et al. | 128/2.06 A |
| 4,478,223 A | 10/1984 | Allor | 128/699 |
| 4,569,357 A | 2/1986 | Sanz et al. | 128/699 |
| 4,587,976 A | 5/1986 | Schmid et al. | 128/699 |
| 4,947,858 A | 8/1990 | Smith | 128/696 |
| 5,312,446 A | 5/1994 | Holschbach et al. | 607/9 |
| 5,331,966 A | 7/1994 | Bennett et al. | 128/696 |
| 5,458,116 A | 10/1995 | Egler | 128/710 |
| 6,049,730 A * | 4/2000 | Kristbjarnarson | 600/509 |
| 6,052,615 A | 4/2000 | Feild et al. | 600/509 |
| 6,115,628 A | 9/2000 | Stadler et al. | 600/517 |
| 6,230,059 B1 | 5/2001 | Duffin | 607/60 |
| 6,358,214 B1 * | 3/2002 | Tereschouk | 600/508 |

FOREIGN PATENT DOCUMENTS

| | | | |
|---|---|---|---|
| EP | 1 273 319 A2 * | 1/2003 | A61N/1/368 |
| WO | WO 02/089901 A2 * | 11/2002 | |

OTHER PUBLICATIONS

Dower et al., "A Clinical Comparison of Three VCG Lead Systems Using Resistance–Combining Networks," *Am. Heart J.*, vol. 55, No. 4, p. 523–34 (Apr., 1958).
Frank, Ernest, "An Accurate, Clinically Practical System For Spatial Vectorcardiography," *Circulation*, vol. XIII, p. 737–49 (May, 1956).

* cited by examiner

*Primary Examiner*—Carl Layno
(74) *Attorney, Agent, or Firm*—Girma Wolde-Michael

(57) ABSTRACT

Implantable medical devices (IMDS) are adapted for developing a vectorcardiograph (VCG) from signals across pairs of electrodes. Sense amplifiers of the IMD are calibrated to correlate the signals to reference sagittal, horizontal and frontal planes of the body. Polar coordinate data is plotted over the time of occurrence of the sensed PQRST electrogram as at least one of an x-axis vector projected into the reference sagittal plane as a sagittal VCG, a y-axis vector projected into the reference horizontal plane as a horizontal VCG, a z-axis vector projected into the reference frontal plane as a frontal VCG, and an xyz-vector in 3-D space. The VCG loops plotted by each of the vectors can also be derived. Thresholding and template matching techniques determine one or more of the maximum vector magnitude and orientation, average axis vector magnitude and orientation, the loop shape, and the loop area representing a particular heart rhythm.

46 Claims, 16 Drawing Sheets

$X_P$-vector [sinus rhythm]

$X_P$-vector [supraventricular tachycardia]

$X_P$-vector [ventricular tachycardia]

METHOD AND APPARATUS FOR DEVELOPING A VECTORCARDIOGRAPH IN AN IMPLANTABLE MEDICAL DEVICE

CROSS-REFERENCE TO RELATED APPLICATION

Reference is hereby made to commonly assigned, co-pending U.S. patent application Ser. No. 09/999,890 filed on even date herewith for METHOD AND APPARATUS FOR DISCRIMINATING BETWEEN TACHYARRHYTHMIAS BY Bozidar Ferek-Petric.

FIELD OF THE INVENTION

This invention relates to cardiac implantable medical devices (IMDs) particularly adapted for developing a vectorcardiograph (VCG) from vector lead signals developed across selected pairs of implanted electrodes.

BACKGROUND OF THE INVENTION

The mechanical events of the heart are preceded and initiated by the electrochemical activity of the heart (i.e., the propagation of the action potential). In the healthy heart, the electrical and mechanical operation of the heart is regulated by electrical signals produced by the heart's sino-atrial (SA) node. Each signal produced by the SA node spreads across the atria, causing the depolarization and contraction of the atria, and arrives at the atrioventricular (A–V) node. The signal is then conducted to the "Bundle of His" during which time it is slowed down to allow for the atrium to pump blood into the ventricles and thereafter to the "Bundle Branches" and the Purkinje muscle fibers of the right and left ventricles. The signals propagated through the Bundle Branches effects depolarization and accompanying contraction of the left ventricle and the right ventricle in close order. Following contraction, the myocardial cells repolarize during a short period of time, returning to their resting state. The right and left atria refill with venous and oxygenated blood, respectively, until the cardiac cycle is again commenced by a signal originating from the SA node. At rest, the normal adult SA node produces a signal approximately 60 to 85 times a minute, causing the heart muscle to contract, and thereby pumping blood to the remainder of the body. The electrical signal passes through the heart chambers as a wave front that can be characterized as a plane advancing from cell to cell through the cardiac muscle that separates cells of different electrical potential as a function of the time that it takes to complete the cardiac cycle.

The above-described cardiac cycle is disrupted in diseased or injured hearts, and the chronic or episodic disrupted electrical activity has long been employed to diagnose the state of the heart. A variety of techniques have been developed for collecting and interpreting data concerning the electrical activity of the heart both in the clinical setting and by way of portable external monitors carried by or IMDs implanted in an ambulatory patient to collect data relating to electrical heart function during daily activities of the patient. Such techniques include electrocardiography, vectorcardiography and polarcardiography.

The most commonly used of these techniques is the electrocardiograph (ECG) machine that displays one-dimension tracings of electrical signals of the heart as the depolarization wave front advances across the heart chambers in the cardiac cycle. An ECG machine typically measures and displays and/or records the voltages at various skin electrodes placed about the body relative to a designated "ground" electrode. The paired electrodes are referred to as "leads" and the lead signal is displayed or printed as an ECG lead tracing. The term "lead" would appear to indicate a physical wire, but in electrocardiography, "lead" actually means the electrical signal or vector in space between a designated pair of skin electrodes arranged as described below, wherein the vectors traverse the heart disposed between the skin electrodes.

The cardiac cycle as displayed in an ECG lead tracing reflects the electrical wave front as measured across one such ECG lead, as shown in U.S. Pat. No. 4,587,976, for example, and depicted in FIG. 1. The portion of a cardiac cycle representing atrial depolarization is referred to as a "P-wave." Depolarization of the ventricular muscle fibers is represented by "Q", "R", and "S" points of a cardiac cycle. Collectively these "QRS" points are called an "R-wave" or a "QRS complex." Re-polarization of the depolarized heart cells occurs after the termination of another positive deflection following the QRS complex known as the "T-wave." The QRS complex is the most studied part of the cardiac cycle and is considered to be the most important for the prediction of health and survivability of a patient. However, the time relation of the P-wave to the QRS complex and the height and polarity of the T-wave and S–T segment are also indicators of a healthy or diseased heart. The S–T segment of a healthy heart is usually isoelectric, i.e., neither positive nor negative in deflection from baseline of the ECG lead tracing. This S–T segment is a most important indicator of the health of the ventricular myocardium and is elevated in ischemia and due to infarctions disrupting the depolarization wave front.

The ECG machine typically plots each ECG lead in parallel over an interval of time such that the heart's electrical activity for one or more cardiac cycles is displayed as parallel ECG lead tracings on a visual display screen and/or printed for purposes of monitoring or analysis. The most common ECGs are known as the "12 lead", the "18 lead," and a variety of other, fewer, lead combinations that simulate the more complete ECGs.

The 12-Lead system provides much redundant information in the frontal (X, Y) plane and transverse (X, Z) plane of the ECG vector signal. It permits only a rough visual estimate of the vector direction in theses two planes. Moreover, the number of skin electrodes and the bulk of the cables and the ECG machine make 12-lead and 18-lead ECG systems only practical in the clinical setting and impractical for use in a portable monitor for chronic use by a patient. Portable ECG recorders or "Holter monitors" therefore employ fewer cables and electrodes to record at least certain of the above-listed ECG lead tracings.

In order to better explain the novel aspects and unique benefits of the present invention, a brief explanation of vectorcardiography and the numerous steps and processes a physician typically undergoes in order to offer a somewhat accurate diagnosis is relevant.

Vectorcardiography uses a vector description of the progress of the depolarization wave front through the heart during the P-wave or loop, the QRS wave or loop and the T-wave or loop as described and illustrated in U.S. Pat. No. 4,587,976, for example, particularly in reference to FIGS. 1 and 2 thereof. Vectorcardiography abandons the one dimension time coordinate of the ECG in favor of plots or tracings of the orientation and magnitude of the vector of the depolarization wave front on each of three planes: a vertical, frontal (X,Y) plane plotting an X-axis (right side or arm to left side or arm) against a Y-axis (head to foot); a horizontal or transverse (X,Z) plane plotting the X-axis against a Z-axis (anterior-posterior); and a vertical, sagittal (Y,Z) plane plotting the Y-axis against the Z-axis as shown in FIG. 2. The resultant xyz-vector is often characterized as comprising the mean P-wave vector, the mean QRS vector and the mean T-wave vector over a cardiac cycle. Each xyz-vector traces a loop during the time of occurrence of the P-wave, QRS complex and T-wave of FIG. 1. In simplified terms, at least three orthogonal ECG signals are simultaneously obtained from at least three orthogonal ECG leads that are generally co-planar with the frontal X,Y plane, the transverse X,Z plane, and the sagittal Y,Z plane. Signal pairs are combined to form the frontal X,Y plane vector or z-vector, the transverse or horizontal X,Z plane vector or y-vector, and the sagittal Y,Z plane vector or x-vector as shown in FIG. 2. The visual presentation and measurement of the xyz-vector in 3-D space is difficult. Consequently, the planar x-vector, y-vector and z-vector are typically simultaneously displayed employing three CRT displays or a split screen CRT display. The trained physician viewing the displays can diagnose the state of the heart from distinctive characteristics of the displayed planar vectors.

Calculations of planar x-vector, y-vector and z-vector and a resultant xyz-vector from lead systems are set forth in U.S. Pat. No. 4,569,357, for example, as referenced in U.S. Pat. No. 4,587,976. Systems for developing and displaying the xyz-vector from four or six ECG skin electrodes are disclosed in U.S. Pat. Nos. 4,478,223 and 5,458,116. A 3-D display of the xyz-vector is disclosed in U.S. Pat. No. 6,052,615.

Referring again to FIG. 2, the right and left ventricles are depolarized typically within a period of about 0.08 seconds (one normal QRS interval) and, as a result an electrical force is generated which is characterized by a QRS vector which depicts both the size and direction of the electrical force at any point in time. The normal plane for the QRS vector (i.e., the normal plane of activation) is the same as the QRS cycle, i.e., generally perpendicular to the frontal X, Y plane and slanted along the axis of the heart. It has been found that the force and direction of the QRS vector shown in FIG. 2 provides an accurate representation of how the heart is functioning over the period of the QRS interval.

FIG. 2 also depicts the smaller T-wave loop of the composite spatial xyz-vector of a normal heart. The amplitudes and spatial orientations of the T-wave vector and the QRS vector are changed in a characteristic manner in hearts having certain known cardiac disease processes.

The conception of vectorcardiography is attributed to Einthoven who determined that the QRS xyz-vector could be approximated by the z-vector projected into the frontal X, Y plane. Einthoven employed three skin electrodes specifically oriented on the body (right arm RA, left leg LL and left arm LA). The leads between these three electrodes formed a triangle known as Einthoven's triangle. It was postulated that these ECG lead signals could always be related to a single vector in the frontal X,Y plane because a vector can be derived from any two signals added vectorally. For diagnostic purposes, these leads were later graphically translated into a triaxial system. Other leads were subsequently added to the triaxial system (termed unipolar leads—aVR, aVL, and aVF) and a Hexial system was developed. For simplification purposes, the system was displayed on a circle and degrees were later assigned to the various leads of the system.

In order for a physician to determine the mean QRS vector, the physician would line up the various leads around the circle according to their positive or negative sign and magnitude and mark the transition from positive to negative on the circle. This area of transition is typically referred to as the "transition" area which when analyzing a single plane, e.g., the frontal X,Y plane, is represented by a line on the circle which separates the circle into positive and negative halves. The mean QRS vector is positioned at a right angle to the transition line on the positive side.

Using the above methodology, the direction and location of the mean QRS vector on the circle determines how the heart is functioning and allows a physician to ascertain typical heart malfunctions. For example, in a normal adult, the mean QRS vector is usually located between 0° and 90°, i.e., between leads I and aVF on the circle. However, a left axis deviation (LAD) is characterized by the mean QRS vector being located in the 0° to −90° range and with right axis deviation (RAD) the mean QRS vector is located in the 90° to 180° range.

As noted in U.S. Pat. Nos. 4,136,690 and 4,478,223, it has long been known that medically significant VCGs can be produced through the use of such a three-lead system. Previous studies have already indicated merit in the VCG analysis of anomalous and ectopic beats for identifying the site of origin of ectopic beats. Such anomalous beats not only commonly result in alteration of readily apparent direction and magnitude of QRS and T-wave vectors, but also affect the direction of rotation QRS vector forces, often accompanied by abnormal delays of QRS vector inscription. The latter characteristics are not readily apparent in analog ECG signals, and thus the VCG gives additional discriminative data. The adjunctive VCG data complements the analog ECG signal data by providing a visual integrated picture of the electrical activity.

Orthogonal leads to provide these tracings were developed by Ernest Frank (see "An Accurate, Clinically Practical System For Spatial Vectorcardiography", *Circulation* 13: 737, May 1956). Frank experimentally determined the image surface for one individual, and from this proposed a system using seven electrodes on the body, plus a grounding electrode. The conventional letter designations for such electrodes, and their respective positions were:

E at the front midline (anterior or ventral);

M at the back midline (posterior or dorsal);

I at the right mid-axillary line (right side);

A at the left mid-axillary line (left side);

C at a 45° angle between the front midline and the left mid-axillary line;

CR on the neck (cranial), and

F on the left leg.

Most diagnostic vector ECG studies have been carried out using the Frank lead system or a modified McFee lead system. An alternative to the Frank lead system that required only four active electrodes (R (right arm), A, F, E), and that used a resistor network based on Frank's image surface data was proposed in 1958 by G. E. Dower and J. A. Osborne (see "A Clinical Comparison of Three VCG Lead Systems Using Resistance-Combining Networks", *Am Heart J* 55: 523, 1958). However, the X-axis, Y-axis and Z-axis signals produced were sometimes different from those of Frank's lead system, and the RAFE system was not adopted. Other lead systems are disclosed in the above-referenced '116 and '223 patents.

As described in the above-referenced '116 and '690 patents and illustrated in FIG. 2, the tip of the QRS vector which represents the cardiac wave front typically traces an oval or cardioid trajectory or loop during the course of each ventricular depolarization-repolarization of the cardiac cycle. Clinical studies, using data from three-lead VCG systems, have indicated the diagnostic value of the maximal QRS vector and T-wave vector which are the vectors drawn from the starting point of the loop to the farthest points of the QRS and T loops. The maximal vector should not be confused with the mean direction which is the vector equal to the sum of all of the instantaneous vectors. The absolute values of the QRS peak vector, the T-wave peak vector, and their difference are not of prime importance for diagnostic purposes, since the absolute values vary from patient to patient as well as with variations in the positioning of the electrodes on the patient. Instead, in each instance, the departures from the angles normally observed in a given patient are diagnostically significant.

The scalar representation of an abnormal supraventricular complex, particularly if nodal-originating, may appear as a bizarre waveform closely resembling a ventricular-originating arrhythmia. However, the relationship between the depolarization potentials represented by the QRS vector forces and the repolarization potential represented by the T vector forces has been proven to be nearly identical for all supraventricular originating complexes, both normal and abnormal. As a result of this fact, a first condition that can be distinguished is whether the ectopic complex is truly of supraventricular origin, the categorization of which includes the normal S-A node complexes in addition to abnormal atrial and nodal ectopic beats. Thus, it is of utmost importance and utility that the differential vector angle can initially aid in the diagnoses and categorization of supraventricular ectopics, whereas a single (scalar) lead system cannot reliably be used to do so.

Additionally, ventricular ectopic complexes of significantly different points of origin (foci) within the ventricles also display significantly different vector angles. Therefore, further categories can be set up for the purpose of identifying the relative foci of the ectopic events, and to some extent (when the lead configuration and heart position are known), the location of the foci within the heart muscle itself. Ventricular ectopi rarely originate from more than five significantly separate foci, and typically originate from one to three foci. Therefore, considerable simplification can ultimately be achieved in the overall circuit mechanization.

In the '690 patent, two-channel, approximately orthogonal, ECG lead signals are applied to a rectangular-to-polar coordinate converter, which produces two output signals showing respectively the instantaneous magnitude and angle of the vector. Not all of the instantaneous values of the vector angles are of interest, but primarily the vector angles at the instants when the QRS and T complexes reach their peaks. These angles are then subtracted to determine the angular difference between the QRS and T vectors which henceforth are termed "QRS-T angle" or "QRS-T vector angle".

The mean T-vector and the mean P-vector are determined in a similar manner. In fact, physicians have determined that one of the more important elements of graphically illustrating the means QRS vector and the mean T-vector is that the angle between the two vectors can be easily ascertained. This angle relates the forces of ventricular depolarization with the forces of ventricle repolarization. In a normal adult, the angle between the mean QRS vector and the mean T-vector is rarely greater than 60° and most often below 45°.

Similarly, the mean P-vector can be determined. This enables a physician to isolate the location of the electrical direction of the excitation of the cardiac muscle of the atrium.

The above analysis has been described using a single plane, namely the frontal X,Y plane characterized by the superior, inferior, right and left boundaries of the human body. In order for a physician to analyze the overall movement of the heart muscle during depolarization and repolarization, the physician needs to analyze the vector forces along another plane, namely the transverse X,Z plane which is characterized by the posterior, anterior, right and left boundaries of the human body.

Much in the same manner as described above, six leads are positioned about the body to measure the electrical currents across the heart muscle in the transverse X,Z plane. These leads are typically called the precordial leads and are represented as VI–V6, respectively. Using the same methodology as described above with respect to the frontal X,Y plane, the location and direction of the mean QRS vector in the transverse X,Z plane can also be determined.

When the X,Y and X,Z planes are analyzed simultaneously, the mean QRS vector (and the other vectors) projects perpendicularly from the transition "plane" rather than the transition "line" of the single plane system. In other words, when the frontal plane and the horizontal plane are isolated and individually analyzed, the mean QRS transition appears as a line across the diameter of the circle. In actuality, this "line" is actually a "plane" when both systems (frontal and horizontal) are analyzed simultaneously and the mean vectors (QRS, T and P) project perpendicularly from this plane into both systems.

As can be appreciated from the above summary, the analytical process of determining the resultant QRS vector and the other vectors can be quite cumbersome and requires a physician to interpret various graphs and/or solve various formulas which tend only to frustrate the diagnostic process and which can lead to erroneous conclusions if analyzed improperly. For simplicity, most physicians analyze each system individually at first and then combine the results. However, as often is the case, the determination of the mean vectors (QRS, T-wave and P-wave) in one plane is still both time consuming and somewhat confusing. Further, trying to determine how the mean vectors project into two planes and how the angles between the vectors relate can be even more confusing.

Moreover, even if a physician can adequately analyze the various graphs and solve the various formulas to arrive at a diagnosis, 3-D representation of the location of the mean QRS vectors (and the other vectors) must be mentally visualized which requires a high degree of mental agility and can lead to misdiagnosis. Further, mentally visualizing the angles between mean vectors would be virtually impossible for even the most skilled physician. The additional problem of how these vectors change in time over the QRS interval is believed to be nearly impossible to consider by the prior methods.

Thus, although it has long formed a basis for teaching electrocardiography, vectorcardiography has never become widely used. The technique is demanding and the system of electrode placement is different from that required for the ECG. Extra work is required, and it is still be necessary to record a 12-lead ECG separately with a different placement of electrodes. However, the vector representations have been drawn for various cardiac diseases and form the bases upon which a doctor is trained to understand and explain the lead tracings from the various leads in the classic 12-Lead ECG system.

But, it is known that the VCG provides valuable diagnostic information for the initial diagnosis and follow-up of the progression of or improvement with treatment of various cardiac disease states or congenital heart defects. Numerous pathologic states may be diagnosed by means of the vectorcardiography including ischemic heart disease, dilatative cardiomyopathy, hypertrophic cardiomyopathy systolic as well as diastolic load of the ventricles, atrial dilatation and various forms of heart failure. Congenital heart defects are also characterized by specific VCG patterns. The VCG is also employed to precisely diagnose ischemic heart disease and localise the myocardial infarction. Moreover, it can be beneficial in discriminating between various types of arrhythmias, e.g., distinguishing ventricular tachycardias and malignant tachyarrhythmias from supraventricular tachycardias. Various arrhythmias and conduction disturbances such as WPW syndrome and any combination of bundle branch blocks produce specific VCG patterns.

There are many instances where it is desirable to be able to diagnose intermittent spontaneous cardiac arrhythmias in ambulatory patients. Frequently faintness, syncope, and tachyarrhythmia palpitation symptoms cannot be induced and observed by the physician in tests conducted in a clinic. For many years, such patients have been equipped with external ECG monitoring systems, e.g., the patient-worn, real time Holter monitors, that continuously sample the ECG from skin electrodes providing one or more ECG lead and record it over a certain time period. Then, the ECG data must be analyzed to locate evidence of an arrhythmia episode from which a diagnosis can be made.

As described in commonly assigned U.S. Pat. Nos. 5,312,446 and 4,947,858, the externally worn ECG recorders have inherent limitations in the memory capacity for storing sampled ECG and EGM data. Cost, size, power consumption, and the sheer volume of data over time have limited real time external Holter monitors to recording 24-hour segments or recording shorter segments associated with arrhythmias that are felt by the patient who initiates storage.

The use of the externally worn Holter monitor coupled with skin electrodes is also inconvenient and uncomfortable to the patient. The skin electrodes can work loose over time and with movement by the patient, and the loose electrodes generates electrical noise that is recorded with the EGM signal and makes its subsequent analysis difficult. It has long been desired to provide an implantable monitor or recorder that is hardly noticeable by the patient and provides the capability of recording only EGM data correlated with an arrhythmia episode that is automatically detected.

Over the last 40 years, a great many IMDs have been clinically implanted in patients to treat cardiac arrhythmias and other disorders including implantable cardioverter/defibrillators (ICDs) and pacemakers having single or dual chamber pacing capabilities, cardiomyostimulators, ischemia treatment devices, and drug delivery devices. Recently developed implantable pacemakers and ICDs have been provided with sophisticated arrhythmia detection and discrimination systems based on heart rate, the morphology and other characteristics of the atrial and ventricular EGM and other characteristics of the EGM. Most of these IMDs employ electrical leads bearing bipolar electrode pairs located adjacent to or in a heart chamber for sensing a near field EGM or having one of the electrodes located on the IMD housing for sensing a far field, unipolar EGM. In either case, the near field or far field EGM signals across the electrode pairs are filtered and amplified in sense amplifiers coupled thereto and then processed for recording the sampled EGM or for deriving sense event signals from the EGM.

In current IMDs providing a therapy for treating a cardiac arrhythmia, the sense event signals and certain aspects of the sampled EGM waveform are utilized to automatically detect a cardiac arrhythmia and to control the delivery of an appropriate therapy in accordance with detection and therapy delivery operating algorithms. In such cardiac IMDs providing pacing or cardioversion/defibrillation therapies, both analog and digital signal processing of the EGM is continuously carried out to sense the P-wave and/or R-wave events and to determine when a cardiac arrhythmia episode occurs.

For example, a digital signal-processing algorithm is employed to distinguish various atrial and ventricular tachyarrhythmias from one another. When a tachyarrhythmia episode is detected, at least selected EGM signal segments and sense event histogram data or the like are stored on a FIFO basis in internal RAM for telemetry out to an external programmer at a later time. Many of these IMDs are also capable of being operated to sample the near-field EGM across bipolar electrode pairs and the far-field EGM between a lead borne electrode and an IMD housing or can electrode. The IMD can be commanded to transmit real time EGM data of indefinite length via uplink telemetry transmissions to the external programmer when a real time telemetry session is initiated by the medical care provider using the programmer.

Implantable cardiac monitors have also been developed and clinically implanted that employ the capability of recording cardiac EGM data for subsequent interrogation and uplink telemetry transmission to an external programmer for analysis by a physician. The recorded data is periodically telemetry transmitted out to a programmer operated by the medical care provider in an uplink telemetry transmission during a telemetry session initiated by a downlink telemetry transmission and receipt of an interrogation command.

The MEDTRONIC® Reveal™ insertable loop recorder is a form of implantable monitor that is intended to be implanted subcutaneously and has a pair of sense electrodes spaced apart on the device housing that are used to pick up the cardiac far field EGM which in this case is also characterized as a "subcutaneous ECG". The Reveal™ insertable loop recorder samples and records one or more segment (depending on the programmed operating mode) of such far field EGM or subcutaneous ECG signals when the patient feels the effects of an arrhythmic episode and activates the recording function by applying a magnet over the site of implantation. For example, the storage of a programmable length segment of the EGM can be initiated when the patient feels faint due to a bradycardia or tachycardia or feels the palpitations that accompany certain tachycardias.

The most recently stored segment or segments of episode data is transmitted via an uplink telemetry transmission to an external programmer when a memory interrogation telemetry session is initiated by the physician or medical care provider using the programmer. Aspects of the RevealTm insertable loop recorder are disclosed in commonly assigned PCT publication WO98/02209.

More complex implantable monitors and pacemaker implantable pulse generators (IPGs) of this type but having more electrodes arranged in a planar array on the device housing are disclosed in commonly assigned U.S. Pat. Nos. 5,331,966, 6,115,628, and 6,230,059. Three or more electrodes are employed to provide a pair of orthogonal sensed EGM or "subcutaneous ECG" signals at the subcutaneous implantation site. A lead can be employed in a disclosed pacemaker embodiment to locate a bipolar electrode pair in a heart chamber to provide an additional near field EGM sense signal from which the P-wave or R-wave can be sensed (depending on the location of the bipolar electrode pair) and through which pacing pulses can be applied to the atrium or ventricle.

Recording of the near field and far field EGM episode data can be invoked automatically by detection of a bradycardia or satisfaction of tachyarrhythmia detection criteria or can be manually commenced by the patient using an external limited function programmer or can be commenced by the physician using a full function programmer.

Various types of cardiac EGM data are collected in further implantable cardiac monitors or other IMDs having monitoring capabilities including those disclosed in U.S. Pat. Nos. 5,404,877, 5,425,373, 5,497,780, 5,556.419, 5,740,811 and 5,810,739.

However, it does not appear that IMD systems have been utilized to develop VCG information for diagnostic reasons or to distinguish tachyarrhythmias from normal, high rate, sinus rhythms or to detect occurrence or degree of myocardial infarction.

While apparently generally acceptable for their intended purposes, so far as is known, none of the prior art IMDs collects EGM data from which a VCG signal in 3-D xyz-vector format or 2-D projections in the sagittal, frontal and/or horizontal planes that can be stored, displayed or employed for diagnostic purposes.

SUMMARY OF THE INVENTION

Accordingly, the present invention provides an IMD with the capacity of deriving VCGs signifying the progress of the depolarization and repolarization wave front signal through the heart during the PQRST segment of the heart cycle, storing such VCGs in memory, and/or employing characteristics of the VCGs in the determination of the state of health of the heart.

The present invention provides for the derivation of vector magnitude and orientation data (as polar coordinates, for example), of high rate PQRST electrogram segments of heart cycles. The polar coordinate data can be mathematically plotted over the time of occurrence of the sensed PQRST electrogram as at least one of an x-axis vector projected into the reference sagittal plane as a sagittal VCG, a y-axis vector projected into the reference horizontal plane as a horizontal VCG, a z-axis vector projected into the reference frontal plane as a frontal VCG, and an xyz-vector in 3-D space. The loops plotted by each of the vectors can also be derived.

In accordance with a further aspect of the present invention, a gain factor that compensates for the angular deviation of the internal lead vector out of coplanar relation with the at least one of the reference sagittal, horizontal, and frontal planes of the body that the at least one of the sagittal vectorcardiogram, horizontal vectorcardiogram, and frontal vectorcardiogram is calculated and employed to correct the PQRST electrogram.

The novel elements believed to be characteristic of the present invention are set forth in the appended claims. The invention itself, together with additional objects and attendant advantages, will best be understood by reference to the following detailed description, which, when taken in conjunction with the accompanying drawings, describes presently preferred embodiments.

BRIEF DESCRIPTION OF THE DRAWINGS

Reference is now made to the accompanying detailed drawings of the preferred embodiments in which like reference numerals represent like or similar parts throughout, and wherein.

DETAILED DESCRIPTION OF THE PREFERRED EMBODIMENTS

Figure 3:
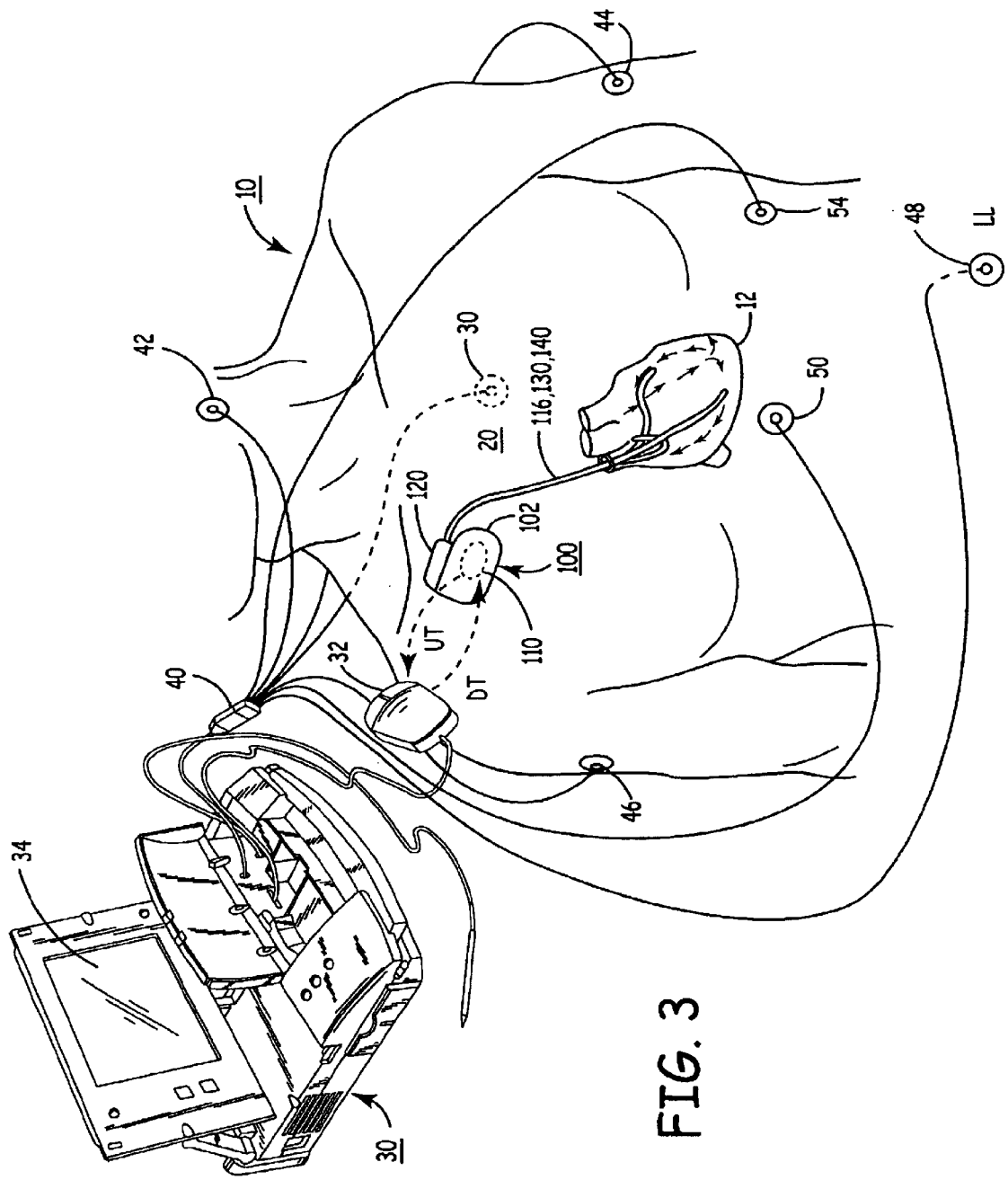
FIG. 3 is a schematic illustration of a cardiac IMD, particularly an ICD, implanted in a patient's body with electrode pairs defining lead vectors and an external programmer in telemetry communication with the IMD and coupled to skin ECG electrodes.

The system of the present invention for providing vectorcardiography through the use of implanted electrodes disposed about the heart 12 is depicted in FIG. 3 in relation to a patient 10, an IMD 20, and an external programmer 30. The IMD 20 could simply be an implantable monitor but is preferably a dual chamber or multi-chamber pacemaker or ICD IPG 100 having electrodes distributed about the heart 12 between which lead vectors can be recorded. For example, the IMD 20 may take the form of an ICD IPG and associated leads of the type described in commonly assigned U.S. Pat. No. 5,776,168 or a bi-atrial and/or bi-ventricular, dual chamber pacing system of the type described in commonly assigned U.S. Pat. Nos. 5,902,324 and 6,219,579 wherein electrodes are located in or about three or four heart chambers or a simpler pacing system as illustrated in the abovereferenced '739 patent, for example.

Figure 4:
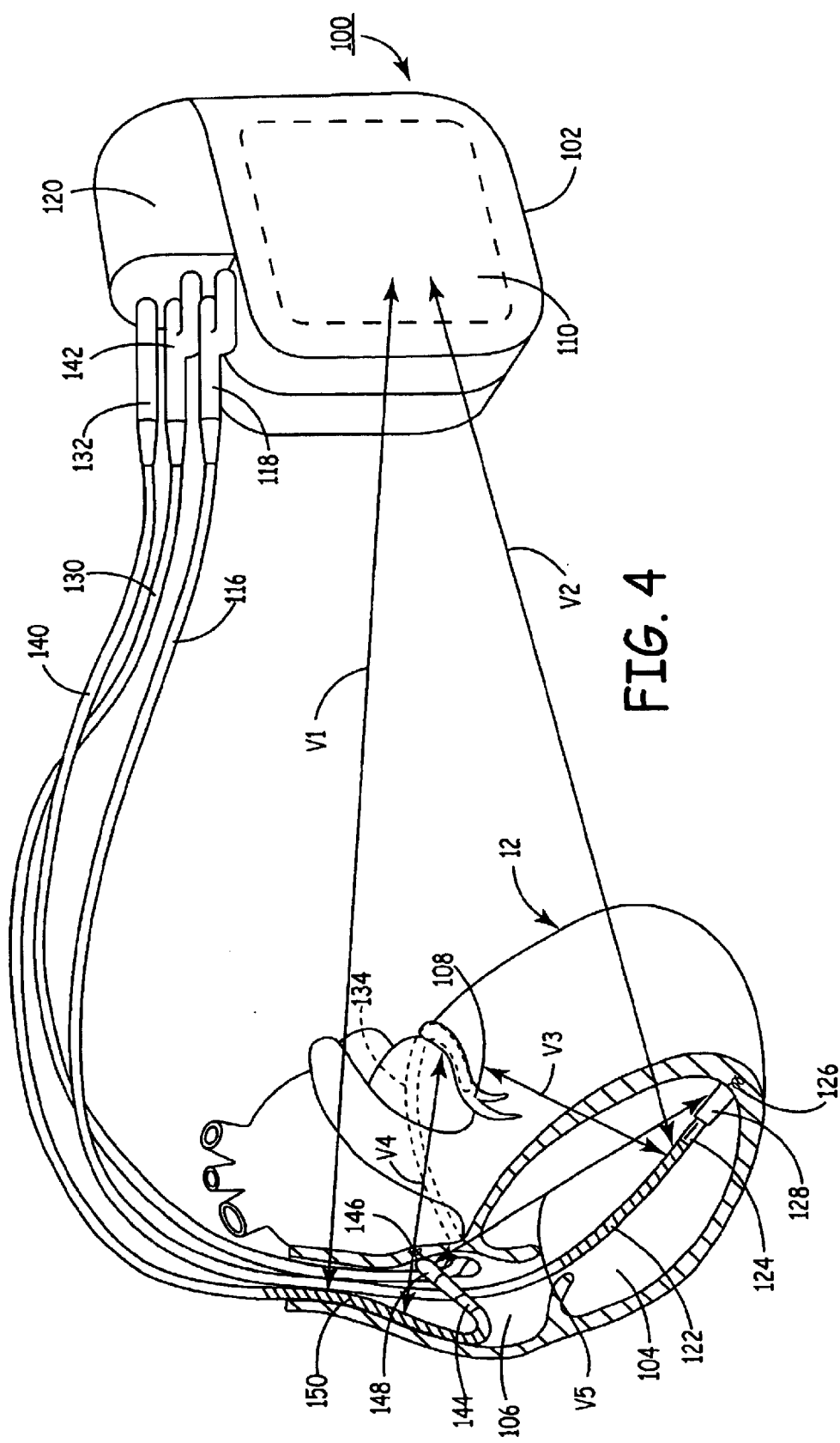
FIG. 4 is a schematic illustration of the an exemplary ICD IPG and lead system for deriving a plurality of EGM vector signals along a like plurality of lead vectors.

In the illustrated example of FIGS. 3 and 4, lead vectors can be recorded by IPG 100 between selected electrode pairs among electrodes on leads 116,130,140, and a can electrode 110 on the hermetic IPG housing 102. The IMD 20 also communicates with a programming head 32 of the external programmer 30 through uplink telemetry (UT) and downlink telemetry (DT) transmissions during a telemetry session initiated by a physician using programmer 30 or automatically initiated in a manner well known in the art.

The external programmer 30 that has the capability of recording external ECG lead vectors between selected pairs of skin electrodes 42, 44, 46, 48, 50 and 52 coupled to programmer 30 through an ECG cable 32 and displaying the vector tracings on the programmer screen 34. A suitable programmer would be the MEDTRONIC® Model 9790 programmer described in U.S. Pat. No. 5,683,432, for example, employing the MEDTRONIC® Vision™ graphic user interface (GUI) display software based upon the IBM's OS/2 operating system having icons and pull down menus for different programming functions. In order to avoid any confusion, the VCG would be displayed within the Vision window exactly as it is used in cardiology practice The xyz-vector loop and the planar projection loops, utilize differing colors for the vector lines for the designating the time by numbers in the conventional manner known in the prior art.

Figure 6:
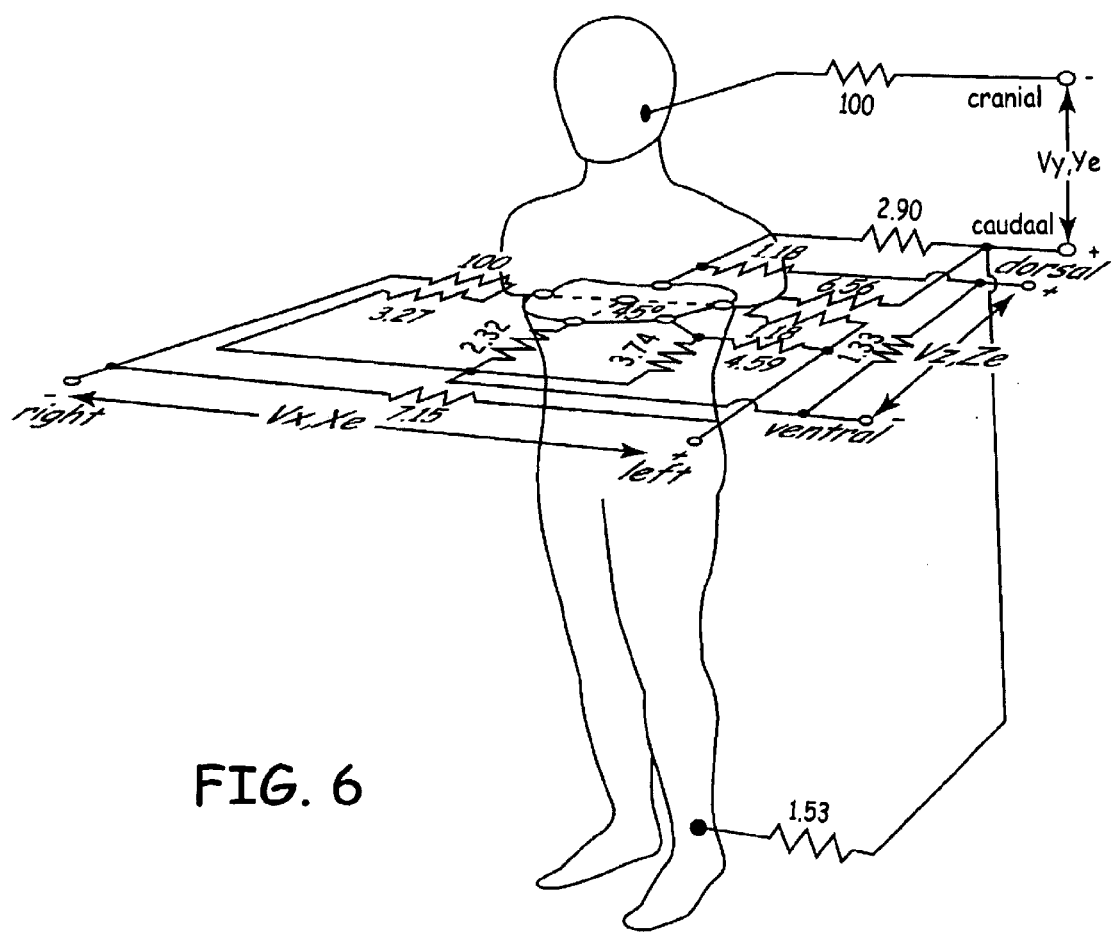
FIG. 6 is a schematic illustration of a Frank lead resistor network employed with ECG skin electrodes for conducting the ECG lead signals from the skin ECG electrodes to develop $X_E$, $Y_E$, and $Z_E$ external vectors in the frontal X,Y plane, the transverse X,Z plane, and the sagittal Y,Z plane, respectively.

The skin electrodes are preferably placed on the patient's body as shown in FIGS. 3 and 6 and are interconnected within programmer 30 via a resistor network as shown in FIG. 6 in a in the manner described by Frank. The LL electrode 48 is a reference electrode that is paired with certain of the other electrodes through the resistor network as shown in FIG. 6.

Figure 5:
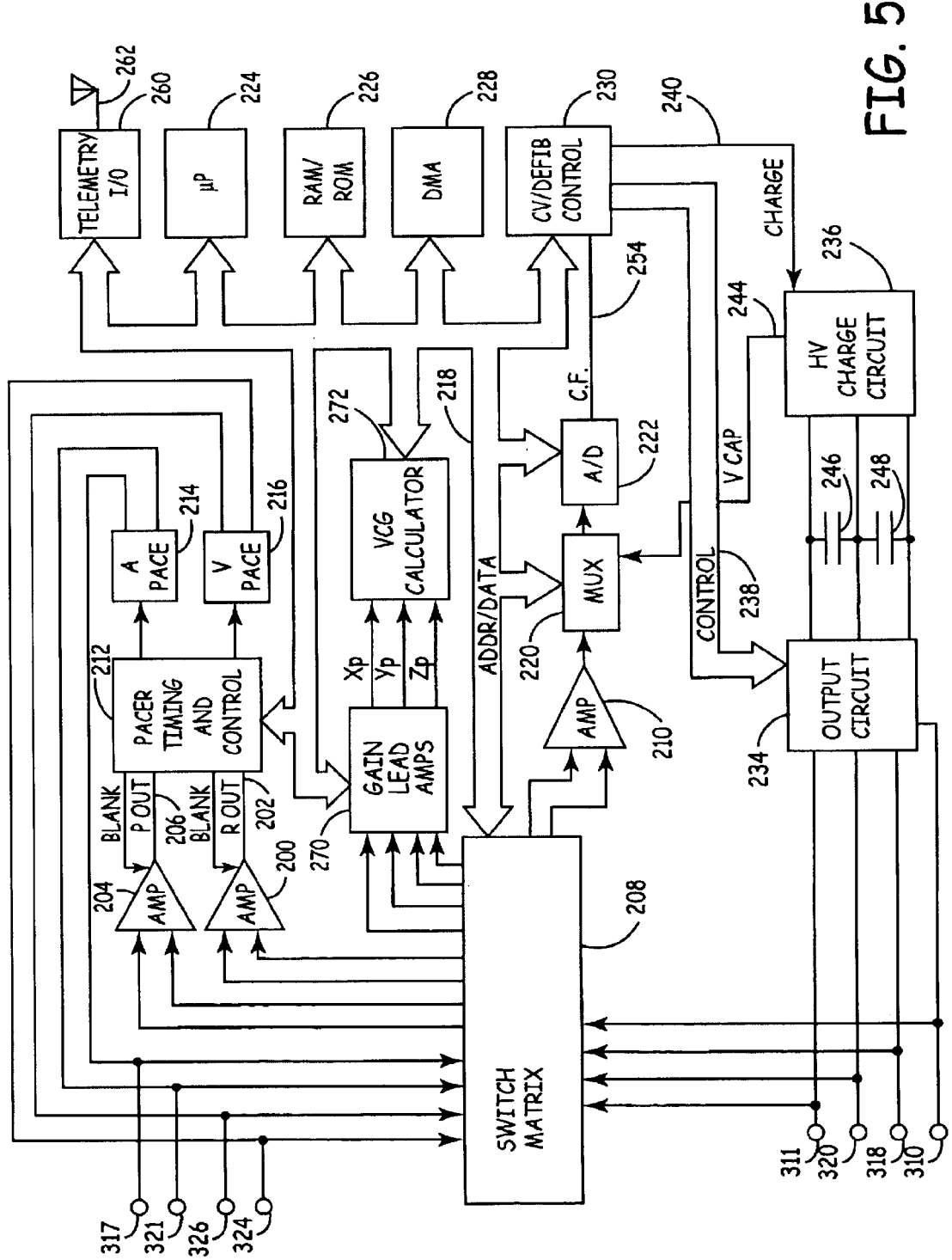
FIG. 5 is a simplified functional block diagram of the ICD IPG of FIG. 4 illustrating the IPG circuitry for deriving the plurality of EGM lead signals, processing the EGM lead signals to develop the $X_p$, $Y_p$, and $Z_p$ planar EGM vectors, processing the $X_p$, $Y_p$, and $Z_p$ planar EGM vectors to derive a 3-D vector, and storing and/or uplink telemetry transmitting the $X_p$, $Y_p$, and $Z_p$ planar EGM vectors and 3-D vector to the external programmer.

FIGS. 4 and 5 illustrate a dual chamber, multi-programmable, ICD IPG 100 and associated lead system for providing atrial and/or ventricular sensing functions for detecting P-waves of atrial depolarizations and/or R-waves of ventricular depolarizations, depending on the programmed pacing and/or sensing mode and delivering pacing or cardioversion/defibrillation therapies in which the present invention may be practiced. Such ICDs include the MEDTRONIC® Gem VR ICD, the Gem DR ICD, the Gem AT ICD, and the InSync™ ICD.

An exemplary defibrillation lead system is depicted in FIG. 4 for delivering cardioversion/defibrillation shock therapies to the atria or ventricles of the heart. FIGS. 4 and 5 are intended to provide a comprehensive illustration of each of the atrial and/or ventricular, pacing and/or cardioversion/defibrillation configurations that may be effected using sub-combinations of the components depicted therein and equivalents thereto.

In the field of automatic implantable arrhythmia control devices, the term "cardioversion" or "cardioverter" refers to the process of, and device for, discharging relatively high-energy electrical shocks into, or across, cardiac tissue to arrest a life-threatening tachyarrhythmia. Cardioversion shocks may, or may not, be synchronized with a cardiac depolarization or rhythm and may be applied to arrest a malignant ventricular or atrial tachycardia or fibrillation with selectable or programmable shock energy. The arrest of fibrillation by such shocks is referred to as "defibrillation" (a form of cardioversion), and "defibrillators" have been characterized as a form of cardioverter. In the context of the present invention, it is to be assumed that these terms are interchangeable, and that use of one term is inclusive of the other device or operation, unless specific distinctions are drawn between them. Current devices or implantable devices for the treatment of tachyarrhythmias, provide programmable staged therapies including anti-tachycardia pacing regimens and cardioversion energy and defibrillation energy shock regimens in order to terminate the arrhythmia with the most energy efficient and least traumatic therapies (if possible), as well as single chamber bradycardia pacing therapies. These devices provide a programmable energy, single polarity waveform, and shock from the discharge of a high voltage output capacitor bank through a pair of electrodes disposed in relation to the heart. The output stage is provided with two separate output capacitor banks, which are sequentially discharged during sequential shock defibrillation and simultaneously discharged during single or simultaneous shock defibrillation through a two or three electrode system.

A right ventricle (RV) lead 116 extending into RV 104 is depicted in a conventional configuration and includes an elongated insulating lead body, enclosing three concentric, electrically isolated, coiled wire conductors, separated from one another by tubular insulating sheaths. A pace/sense ring electrode 124 and a helical, pace/sense electrode 126 that is mounted retractably within an insulating electrode head 128 are located adjacent the distal end of the RV lead 116. Helical electrode 126 is adapted to be extended out of the electrode head 128 and screwed into the ventricular apex in a manner well known in the art. RV pace/sense electrodes 124 and 126 are each coupled to a coiled wire conductor within the RA lead body and are employed for cardiac pacing in the ventricle and for sensing near-field R-waves. RV lead 116 also supports an elongated, exposed wire coil, defibrillation electrode 122 in a distal segment thereof adapted to be placed in the right ventricle 104 of heart 102. The RV defibrillation electrode 122 may be fabricated from platinum, platinum alloy or other materials known to be usable in implantable defibrillation electrodes and may be about 5 cm in length. Defibrillation electrode 122 is also coupled to one of the coiled wire conductors within the lead body of RV lead 116. A bifurcated connector end 118 at the proximal end of the RA lead body has three exposed electrical connectors, each coupled to one of the coiled conductors, that are attached within the connector block 120 to connector block terminals in a manner well known in the art.

A coronary sinus (CS) lead 130 extending into CS and great vein 108 includes an elongated insulating lead body enclosing one elongated coiled wire conductor coupled to an elongated exposed coil wire defibrillation electrode 134. CS defibrillation electrode 134, illustrated in broken outline, is located within the coronary sinus and great vein 108 of the heart 102 and may be about 5 cm in length. A connector end 132 at the proximal end of the CS lead 130 has an exposed connector coupled to the coiled wire conductor and is attached within the connector block 120 to connector block terminals in a manner well known in the art. The CS lead 130 can include one or more pace/sense electrode adapted to be located deep within the great vein 108 for pacing the left ventricle and sensing depolarizations traversing the left ventricular wall.

The right atrial/superior vena cava (RA/SVC) lead 140 extending into the right atrium 106 includes an elongated insulating lead body enclosing three concentric, electrically isolated, coiled wire conductors separated from one another by tubular insulating sheaths, corresponding generally to the structure of the RV lead 116. The lead body is formed in a manner well known in the art capable of assuming an atrial J-shape in order to position its distal end in the right atrial appendage. A pace/sense ring electrode 144 and an extendable helical, pace/sense electrode 146, mounted retractably within an insulating electrode head 148, are formed distally to the bend of the J-shape. Helical electrode 146 is adapted to be extended out of the electrode head 148 and screwed into the atrial appendage in a manner well known in the art. Pace/sense electrodes 144 and 146 are employed for atrial pacing and for near-field sensing of P-waves. An elongated, exposed coil defibrillation RA/SVC electrode 150 is supported on RA/SVC lead 140 extending proximally to pace/sense ring electrode 144 and coupled to the third coiled wire conductor within the RA/SVC lead body. Electrode 150 preferably is 10 cm in length or greater and is configured to extend from within the SVC and toward the tricuspid valve. A bifurcated connector 142 located at the proximal end of the RA/SVC lead 140 carries three exposed electrical connectors, each coupled to one of the coiled wire conductors, that are attached within the connector block 120 to connector block terminals in a manner well known in the art.

In the preferred embodiment of FIGS. 4 and 5, depending on the programmed pacing mode, pacing pulses may be applied to the right atrium and right and/or left ventricle in response to the detection of the appropriate bradycardia condition by the ICD IPG 100. The pacing and sensing functions are effected through the atrial and ventricular bipolar pace/sense electrode pairs at the ends of RA/SVC lead 140 and RV lead 116, respectively, fixed in the right atrium 106 and right ventricle 104, respectively, that are electrically coupled to the circuitry of IPG 100 through a connector block 120. Delivery of cardioversion or defibrillation shocks to the atrial and/or ventricular chambers of the heart 12 may be effected through selected combinations of the illustrated exemplary defibrillation electrodes 122, 150, and 134 as well as an exposed surface electrode 110 of the outer housing or can of the IPG 100. The can electrode 110 optionally serves as a subcutaneous defibrillation electrode, used as one electrode optionally in combination with one intracardiac defibrillation electrode for cardioverting or defibrillating either the atria or ventricles. A remote, subcutaneous defibrillation patch electrode may be provided in addition to or substitution for the can electrode 110.

The recording of internal planar lead vectors $X_p$, $Y_p$, and $Z_p$ to develop the internal VCG of the present invention can be practiced employing selected pairs of these electrodes located in the RV 104, right atrium 106 and CS/great vein 108 as well as the can electrode 110. The present invention can be practiced in any pacing or ICD system having such electrodes implanted about the heart 12 to provide lead vectors or a greater or lesser number of such electrodes providing a greater or lesser number of lead vectors. FIG. 4 illustrates a number of such possible lead vectors including: (1) lead vector V1 between one or more of the RA/SVC electrodes 144/146/150 and can electrode 110; (2) lead vector V2 between one or more of the RV electrodes 122/124/126 and can electrode 110; (3) lead vector V3 between CS electrode 134 (or a pace/sense electrode if present on CS lead 140) and one or more of the RV electrodes 122/124/126; (4) lead vector V4 between CS electrode 134 (or a pace/sense electrode if present on CS lead 140) and one or more of the RA electrodes 124/146/150; and (5) lead vector V5 between one or more of the RV electrodes 122/124/126 and one or more of the RA electrodes 124/146/150.

An exemplary dual chamber ICD operating system in which the present invention may be implemented is shown schematically in FIG. 5. The ICD IPG circuitry of FIG. 5 includes a high voltage section for providing relatively high voltage cardioversion/defibrillation shocks when needed in response to detection of a tachyarrhythmia and a low voltage pace/sense section for sensing P-waves and/or R-waves and providing relatively low voltage bradycardia pacing and anti-tachycardia pacing therapies as well as developing the VCG in accordance with the present invention. The high voltage and low voltage circuitry are operated under the control of a microcomputer including a microprocessor 224, ROM/RAM 226 and DMA 228. Telemetry transceiver I/O 260 and antenna 262 communicate with external programmer 30 in UT and DT telemetry transmissions of a telemetry session for interrogating ICD data or programming ICD operating modes and parameters in a manner well known in the art.

The block diagram of FIG. 5 depicts the atrial and ventricular pace/sense and defibrillation lead connector terminals of the connector block 120. Assuming the electrode configuration of FIG. 2, the correspondence to the illustrated leads and electrodes is as follows: Optional terminal 310 is hard wired to electrode 110, that is, the un-insulated portion of the housing of the PCD IPG 100, and technically may be directly connected and not be part of the connector block 120. Terminal 320 is adapted to be coupled through RV lead 116 to RV cardioversion/defibrillation electrode 122. Terminal 311 is adapted to be coupled through RA lead 140 to RA/SVC electrode 150. Terminal 318 is adapted to be coupled through CS lead 130 to CS defibrillation electrode 134. However, it will be understood that fewer terminals may be provided than depicted, and/or that one or more differing defibrillation leads, e.g., epicardial patch electrode and subcutaneous patch electrode bearing leads may also be employed for one or more of the depicted defibrillation electrode bearing leads.

Terminals 310, 311, 318 and 320 are coupled to high voltage output circuit 234. High voltage output circuit 234 includes high voltage switches controlled by CV/DEFIB CONTROL logic 230 via control bus 238. The switches within circuit 234 control which electrodes are employed and which are coupled to the positive and negative terminals of the capacitor bank including capacitors 246 and 248 during delivery of the intermediate and high voltage cardioversion and defibrillation shocks.

Terminals 324 and 326 of the connector block are adapted to be coupled through RV lead 116 to RV pace/sense electrodes 124 and 126 for sensing and pacing in the ventricle. Terminals 317 and 321 are adapted to be coupled through RA/SVC lead 140 to RA pace/sense electrodes 144 and 146 for sensing and pacing in the atrium. Terminals 324 and 326 are coupled to the inputs of R-wave sense amplifier 200 through switches in switch network 208. R-wave sense amplifier 200 preferably takes the form of an automatic gain controlled amplifier providing an adjustable sensing threshold as a function of the measured R-wave signal amplitude. A ventricular sense event or VSENSE signal is generated on R-OUT line 202 whenever the signal sensed between electrodes 124 and 126 exceeds the current ventricular sensing threshold. Terminals 317 and 321 are coupled to the P-wave sense amplifier 204 through switches in switch network 208. P-wave sense amplifier 204 preferably also takes the form of an automatic gain controlled amplifier providing an adjustable sensing threshold as a function of the measured P-wave amplitude. An atrial sense event or ASENSE signal is generated on P-OUT line 206 whenever the signal sensed between pace/sense electrodes coupled to terminals 317, 321 exceeds the current atrial sensing threshold. The A-PACE and V-PACE output circuits 214 and 216 are also coupled to terminals 317, 321 and 324, 326, respectively. The atrial and ventricular sense amplifiers 204 and 200 are isolated from the A-PACE and V-PACE output circuits 214 and 216 by appropriate isolation switches within switch matrix 208 and also by blanking circuitry operated by A-BLANK and V-BLANK signals during and for a short time following delivery of a pacing pulse in a manner well known in the art. The general operation of the R-wave and P-wave sense amplifiers 200 and 204 may correspond to that disclosed in U.S. Pat. No. 5,117,824.

The ICD IPG circuitry of FIG. 5 provides atrial and/or ventricular cardiac pacing for bradycardia and tachycardia conditions and synchronized cardioversion and defibrillation shock therapies for tachyarrhythmias in accordance with therapy regimes programmed by the physician. With respect to the pacing operations, the pacer timing and control circuitry 212 includes programmable digital counters which control the basic time intervals associated with bradycardia pacing modes including DDD, VVI, DVI, VDD, AAI, DDI and other modes of single and dual chamber pacing well known to the art. Pacer timing and control circuitry 212 also controls escape intervals associated with timing and delivering anti-tachyarrhythmia pacing in both the atrium and the ventricle, employing any anti-tachyarrhythmia pacing therapies known to the art. In the process, pacer timing and control circuitry 212 also times the operation of and processes ASENSE and VSENSE events on the P-OUT and R-OUT lines of the atrial and ventricular sense amplifiers 204 and 200.

In normal pacing modes of operation, intervals defined by pacer timing and control circuitry 212 include atrial and ventricular pacing escape intervals, blanking intervals, the refractory periods during which sensed P-waves and R-waves are ineffective to restart timing of the escape intervals, and the pulse widths of the pacing pulses. These intervals are determined by microprocessor 224, in response to stored data in RAM in ROM/RAM 226 and are communicated to the pacer timing and control circuitry 212 via address/data bus 218. Pacer timing and control circuitry 212 also determines the amplitude of the cardiac pacing pulses under control of microprocessor 224.

During pacing, the escape interval counters within pacer timing and control circuitry 212 are reset upon sensing of R-waves and P-waves as indicated by a signals on lines 202 and 206. In accordance with the selected pacing mode, pacer timing and control circuitry 212 provides pace trigger signals to the A-PACE and V-PACE output circuits 214 and 216 on timeout of the appropriate escape interval counters to trigger generation of atrial and/or ventricular pacing pulses. The pacing escape interval counters are also reset on generation of pacing pulses, and thereby control the basic timing of cardiac pacing functions. The value of the counts present in the escape interval counters when reset by sensed R-waves and P-waves may be used as measures of the durations of R-R intervals, P-P intervals, P-R intervals and R-P intervals, which measurements are stored in RAM in ROM/RAM 226 and used to detect the presence of tachyarrhythmias.

Microprocessor 224 operates as an interrupt driven device, and is responsive to interrupts from pacer timing and control circuitry 212 corresponding to the occurrence of sensed P-waves (ASENSE) and R-waves (VSENSE) and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P internal) may be stored. Preferably, a portion of RAM in the ROM/RAM 226 is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. In the event that an atrial or ventricular tachyarrhythmia is detected, and in anti-tachyarrhythmia pacing regimen is prescribed, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

Microprocessor 224 activates cardioversion/defibrillation control circuitry 230, which initiates charging of the high voltage capacitors 246 and 248 via charging circuit 236, under control of high voltage charging control line 240 in response to the detection of atrial or ventricular fibrillation or tachyarrhythmia requiring a cardioversion shock. The voltage on the high voltage capacitors is monitored via VCAP line 244 and applied to multiplexer 220, A/D converted in A/D converter/comparator 222 and compared to a predetermined value set by microprocessor 224 resulting in generation of a logic signal on Cap Full (OF) line 254, terminating charging. Thereafter, timing of the delivery of the defibrillation or cardioversion shock is controlled by pacer timing/control circuitry 212. The microprocessor 224 returns the operating mode to cardiac pacing and awaits the next successive interrupt due to pacing or the occurrence of a sensed atrial or ventricular depolarization following delivery of the fibrillation or tachycardia therapy.

Delivery of the cardioversion or defibrillation shocks is accomplished by output circuit 234, under control of control circuitry 230 via control bus 238. Output circuit 234 determines whether a monophasic or biphasic shock is delivered, the polarity of the electrodes and which electrodes are involved in delivery of the shock. Output circuit 234 also includes high voltage switches that control whether electrodes are coupled together during delivery of the shock. An example of output circuitry for delivery of biphasic shock regimens to multiple electrode systems may be found in U.S. Pat. No. 4,727,877.

Ventricular defibrillation may be accomplished using higher shock energy levels than required for atrial defibrillation and may employ the same or a different electrode set. For example, terminals 310, 311, 318 and 320 or only terminals 311, 318 and 320 may be employed for atrial defibrillation. Terminals 311, 320 and 310 might be employed for ventricular defibrillation, with terminal 311 (coupled to RA/SVC electrode 150) coupled to terminal 310 (can electrode 110). Alternatively, terminals 310, 318 and 320 may be employed, with terminal 318 (coupled to CS electrode 134) coupled to terminal 310. As a further alternative, terminals 311, 310, 318 and 320 might all be employed for ventricular defibrillation, with terminals 310, 311 and 320 coupled in common. As yet another alternative, only terminals 310 and 320 might be employed for ventricular defibrillation added or substituted for either of terminals 311 or 318 for treating ventricular fibrillation.

In modern ICD IPGs, the particular therapies are programmed in during a patient work up by the physician, and a menu of therapies is typically provided. For example, on initial detection of an atrial or ventricular tachycardia, an anti-achycardia pacing therapy may be selected and delivered to the chamber in which the tachycardia is diagnosed or to both chambers. On re-detection of tachycardia, a more aggressive anti-tachycardia pacing therapy may be scheduled. If repeated attempts at anti-tachycardia pacing therapies fail, a higher-level cardioversion shock may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion shocks if the rate of the detected tachycardia is above a preset threshold.

In the event that atrial or ventricular fibrillation is identified, the typical therapy is delivery of a high amplitude defibrillation shock, typically in excess of 10 joules in the case of ventricular fibrillation and about 1 joule or less in the case of atrial defibrillation. Lower energy levels are employed for cardioversion. As in the case of currently available ICDs, and as discussed in the above-cited references, it is envisioned that the amplitude of the defibrillation shock may be incremented in response to failure of an initial shock or shocks to terminate fibrillation.

Switch matrix 208 is also used in an EGM sensing and data recording mode to select which of the available pace/sense electrode pairs, or a pace/sense electrode and a further electrode, are coupled to the inputs of wide band (0.5–200 Hz) EGM sense amplifier 210 for use in digital signal storage of the patient's near-field or far-field atrial and ventricular EGM. Therefore, the terminals 317, 321, adapted to be coupled to the atrial pace/sense electrodes 144,146, and the terminals 324, 326, adapted to be coupled to the ventricular pace/sense electrodes 124, 126, are also coupled to the switch matrix 208. Switches within switch matrix 208 are selectively controlled by the microprocessor 224 or circuits within the pacer timing and control circuitry 212, via data/address bus 218, to couple the terminals 317, 321 or 324, 326 to the inputs of EGM amplifier 210 and to thereby apply atrial or ventricular near-field signals to the EGM amplifier 210. Alternatively, the switches are set so that one of the atrial terminal 317 or 321 and the can electrode terminal 310 or one of the ventricular terminals 324 or 326 and the can electrode terminal 310 are coupled to the inputs of EGM amplifier 210 and to thereby apply atrial or ventricular far-field signals to the EGM amplifier 210. Of course, EGM amplifier 210 may be duplicated for the atrial and ventricular channels and for near-field and far-field signal sensing and amplification. In all such cases, the input terminals of the EGM amplifier 210 are protected from the delivery of A-PACE and V-PACE pulses, and the delivery of any cardioversion/defibrillation shocks, in the same manner as the input terminals of the atrial and ventricular sense amplifiers 204 and 200.

The use of the EGM amplifier 210 for this function allows the continued, simultaneous processing of the P-OUT and R-OUT signals of the atrial and ventricular sense amplifiers 204 and 200 by the pacer timing and control circuitry and microprocessor 224 to detect the onset of a tachyarrhythmia and to commence delivery of an appropriate therapy.

The output signals from EGM amplifier 210 are provided to multiplexer 220, and thereafter converted to multi-bit digital signals by A/D converter 222 for storage in RAM in ROM/RAM 226 under control of DMA 228. In this regard, the digitized signals may be temporarily stored in a buffer holding 10 seconds of the digitized EGM on a FIFO basis (preferably, 5 seconds recorded before and after the sensed event). When an SIC is incremented to a predetermined, preferably programmed-in, count, the digitized EGM in the buffer and the associated buffer count and date/time stamp are transferred to a specific storage rolling buffer in RAM in ROM/RAM 228.

Figure 1:
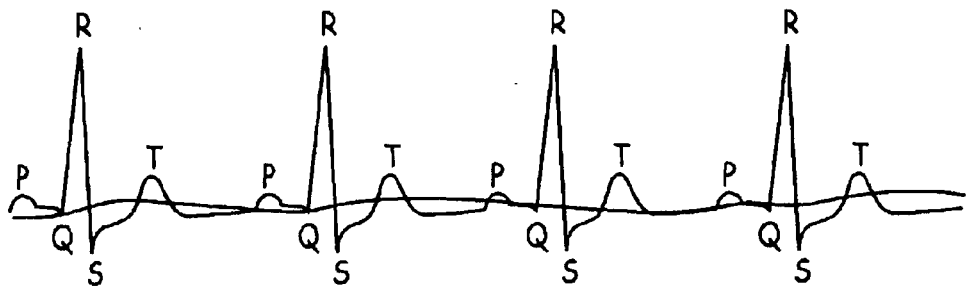
FIG. 1 is an illustration of an exemplary ECG lead tracing.
Figure 2:
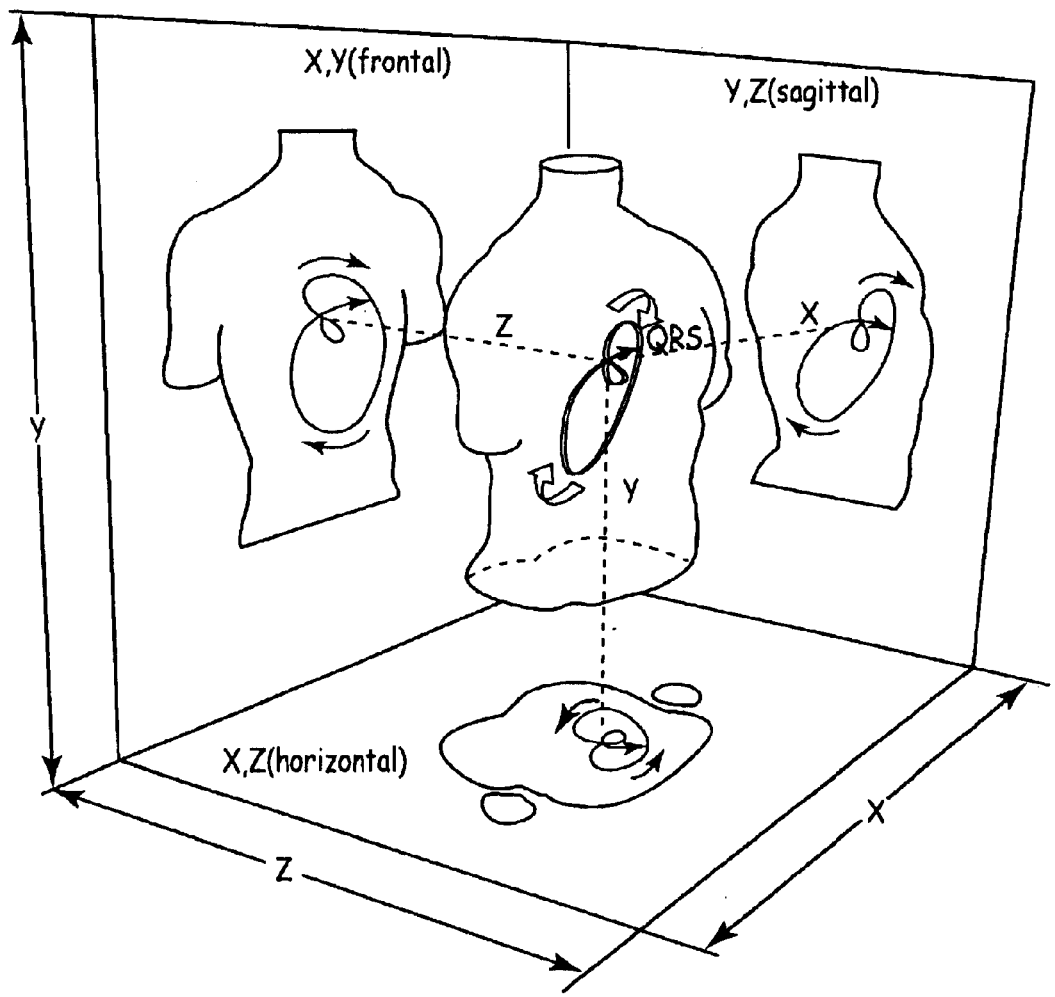
FIG. 2 is a representation of the QRS spatial VCG and its projection onto the frontal X,Y plane, the transverse X,Z plane, and the sagittal Y,Z plane.

To practice the present invention, the ICD circuitry further comprises the lead amplifiers circuit 270 and VCG calculator block 272 that process the EGM leads across selected ones of the vectors V1 through V5 to develop the 3-D xyz-vector or one or more of the planar x-vector, y-vector and z-vector of FIG. 2. The calculations of vectors can take the forms disclosed in the prior art, e.g. those disclosed in the above-referenced '357 and '976 patents. Preferably, polar coordinates of the sampled signals across the vectors V1 through V5 are derived and stored in memory, at least temporarily so that a set of polar coordinate data is developed over the PQRST interval of a selected heartbeat. Each polar coordinate defines a magnitude and orientation (polar direction away from the origin) of the vector. The set of polar coordinate data can effectively be plotted as a VCG loop, and the VCG loop can be displayed and/or analyzed to derive its area. The maximum vector magnitude and orientation as well as an average (or mean) vector can be determined from the set of polar coordinate data.

The calculation of the 3-D xyz-vector can be eliminated from the IMD operating system and more conveniently accomplished within the programmer from at least two of the UT transmitted planar x-vector, y-vector and z-vector. The above-identified electrodes borne by leads 116, 130 and 140 and the can electrode 110 are selectively coupled with lead amplifier inputs by switch matrix 208 in accordance with a programmed selection communicated to switch matrix 208 through bus 218.

Any one or more of the lead vectors V1–V5 of FIG. 4 can be coupled to the inputs of two or more sense amplifiers within the sense amplifiers block 270 to develop the planar x-vector, y-vector and z-vector of FIG. 2. Switch matrix 208 can include a multiplexer to multiplex a single lead vector among the lead vectors V1–V5 of FIG. 4 to the sense amplifiers within the sense amplifiers block 270.

For example, the $X_p$ lead vector could be developed across the lead electrodes 126 and 110 defining the V2 vector, the $Y_p$ lead vector could be developed across the lead electrodes 126 and 146 defining the V5 vector, and the $Z_p$ lead vector could be developed across the lead electrodes 126 and 134 defining the V3 vector. Different combinations lead electrodes could be employed to provide the optimal EGM lead vectors in various patients depending upon the patient's anatomy and the locations of the various electrodes illustrated in FIG. 4. It is necessary to calibrate or normalize the gains of the sense amplifiers within sense amplifiers block 270 coupled to the selected lead electrode pairs so that the planar EGM x-vectors, y-vectors and z-vectors (the $X_p$, $Y_p$, and $Z_p$ EGM lead vectors) that are developed have magnitudes that correspond to the magnitudes of the external ECG x-vectors, y-vectors and z-vectors (the $X_E$, $Y_p$, and $Z_E$ ECG lead vectors). One way of doing so would be to derive each EGM lead vector through a selected EGM sense amplifier, UT transmit the EGM lead vector to the external programmer 30, simultaneously derive the corresponding ECG lead vector, compare the two vectors either visually or automatically to derive the instantaneous difference, and adjust the gain of the selected EGM sense amplifier via a DT transmitted gain adjustment command from the programmer 30 until the difference is minimized.

Figure 7A:
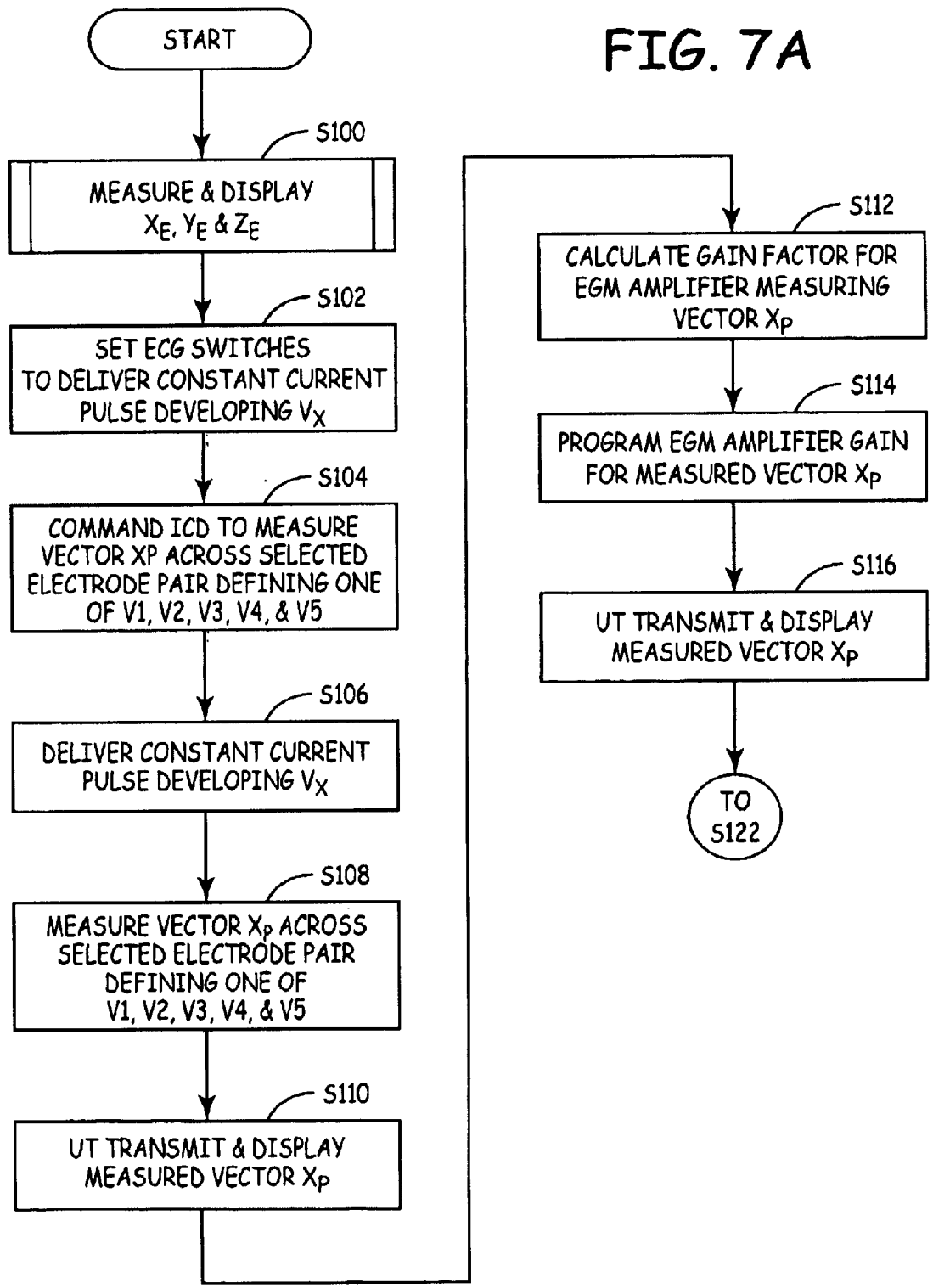
FIGS. 7A–7C is a flow chart of the steps of the calibration algorithm undertaken to correct the gain of each ICD sense amplifier that collectively develop the $X_p$, $Y_p$, and $Z_p$ planar vectors in the frontal X,Y plane, the transverse X,Z plane, and the sagittal Y,Z plane.
Figure 7B:
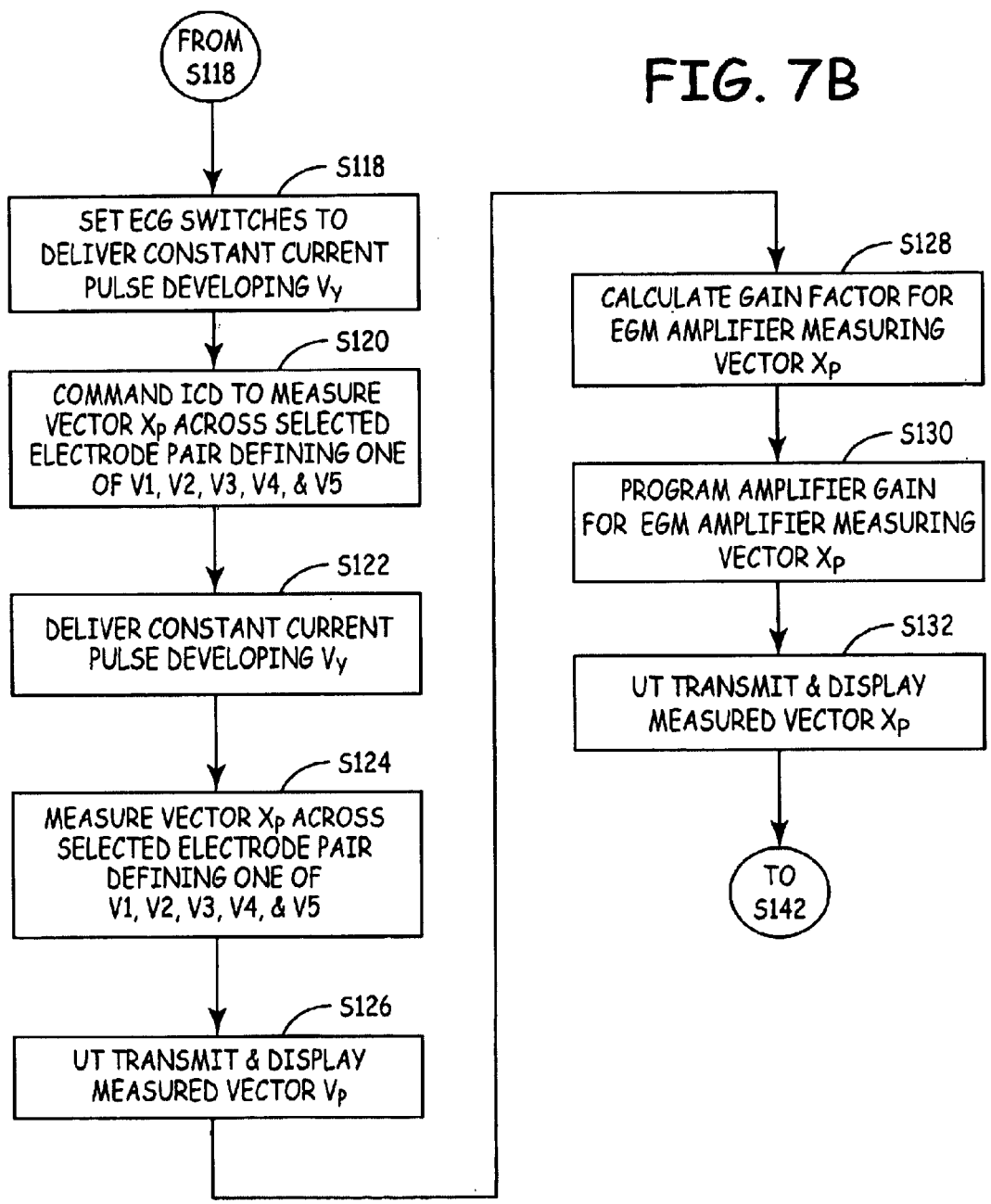
Figure 7C:
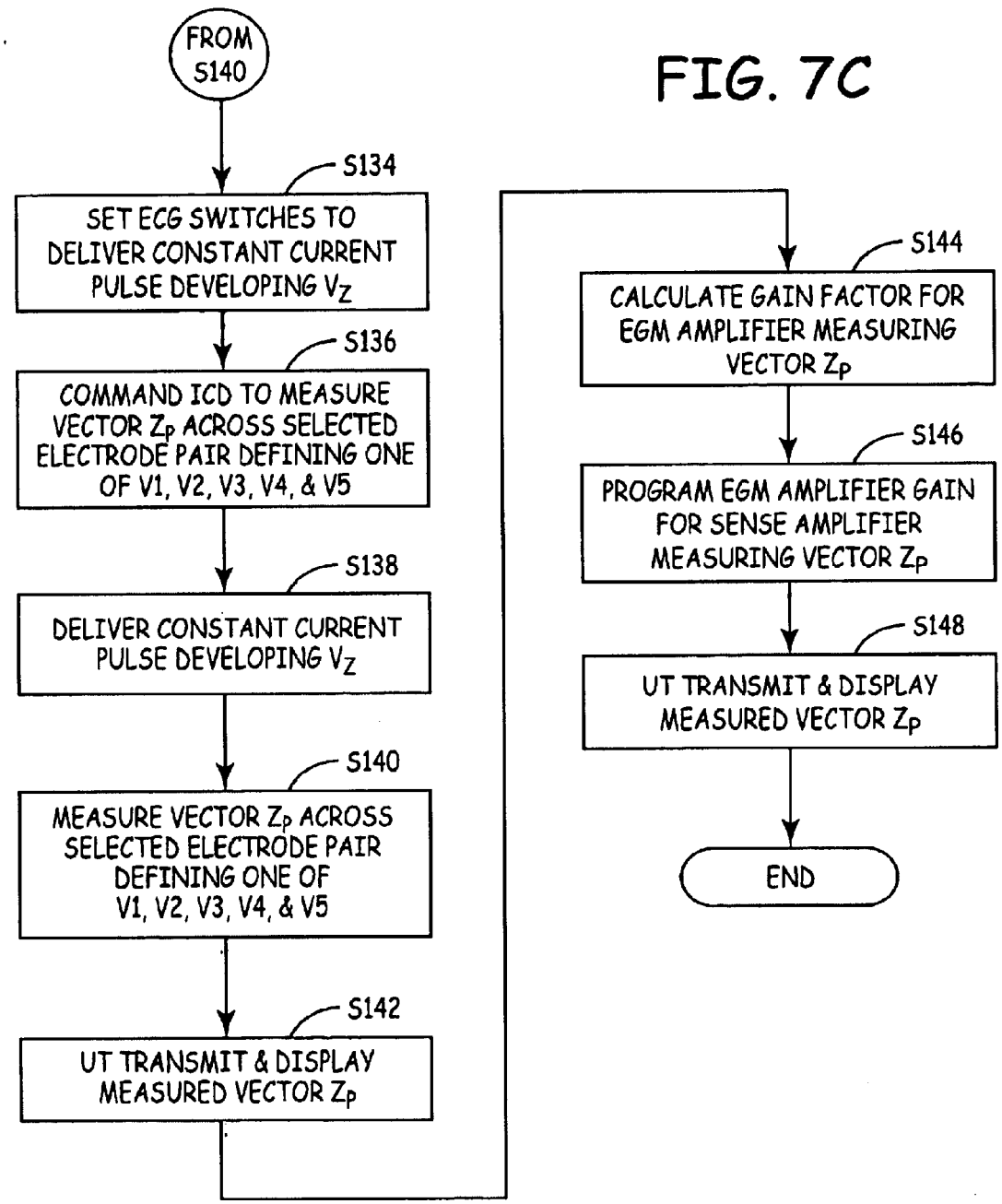

Another way to adjust the gains of the EGM sense amplifiers within sense amplifiers block 270 coupled to the selected lead electrode pairs is accomplished in a calibration algorithm illustrated in FIGS. 7A–7C employing hardware illustrated in FIGS. 3–6 operating as illustrated in FIGS. 8–11.

FIG. 6 is a schematic illustration of a Frank lead resistor network 90 employed with ECG skin electrodes for conducting the ECG lead signals from the skin ECG electrodes to develop $X_E$, $Y_E$, and $Z_E$ external vectors in the frontal X,Y plane, the transverse X,Z plane, and the sagittal Y,Z plane, respectively. The resistor values illustrated in FIG. 6 are the standardized values for Frank leads. The skin electrodes 42–54 are not precisely within the frontal X,Y plane, the transverse X,Z plane, and the sagittal Y,Z planes.

The resistor network 90 compensate for the offset of the skin electrodes out of the frontal X,Y plane, the transverse X,Z plane, and the sagittal Y,Z planes and also corrects for the inhomogeneous tissue of the human torso. The resistor network 90 would not be necessary if the heart were in a cube filled with water and the electrodes were located on the sides of the cube because the electric cardiac vector would spread uniformly to the electrodes. The skin electrodes 42–54 of FIGS. 3 and 6 are obviously not arranged on the sides of a cubic body, and the body itself is not homogeneous in tissues between the heart and the skin electrodes. Therefore, the resistor network 90 is necessary between the skin ECG electrodes 42–54 and the ECG signal processing circuitry of an ECG or VCG machine or a programmer 30.

FIGS. 7A–7C comprise a schematic illustration of the steps of the calibration algorithm undertaken to correct the gain of each ICD sense amplifier among sense amplifiers 270 that collectively develop the $X_p$, $Y_p$, and $Z_p$ EGM lead vectors in the frontal X,Y plane, the transverse X,Z plane, and the sagittal Y,Z plane. The performance of the algorithm following implantation of the ICD IPG 100 involves coordinated UT and DT transmissions between the ICD IPG 100 and the programmer 30.

Figure 8:
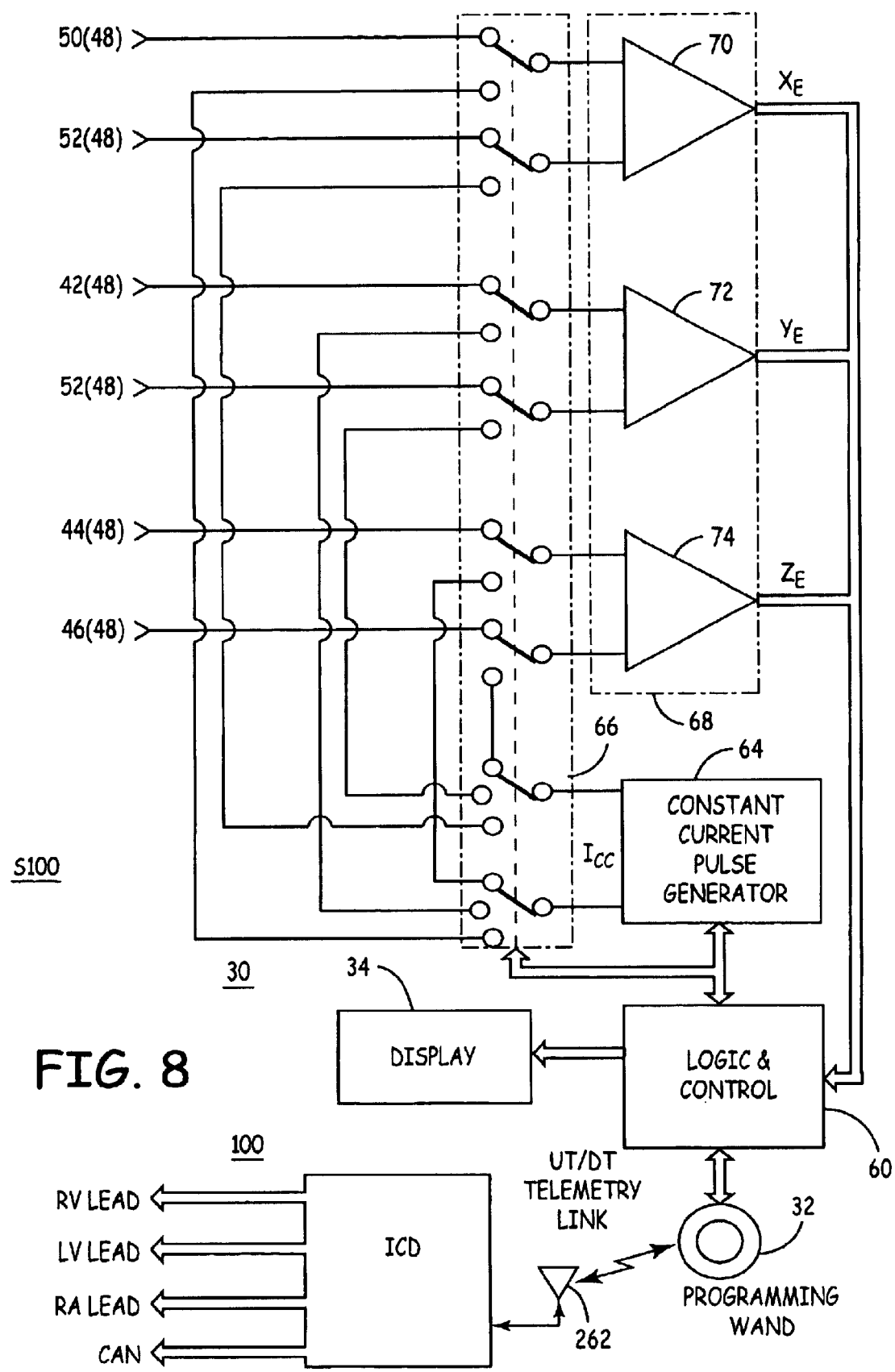
FIG. 8 is a circuit diagram illustrating the setting of a switch network of the external programmer for developing the $X_e$, $Y_e$, and $Z_e$ planar ECG vectors in the frontal X,Y plane, the transverse X,Z plane, and the sagittal Y,Z plane in a step of FIG. 7A.

Step S100 of FIG. 7A is not actually employed in the calibration of the sense amplifiers among sense amplifiers 270 but can be employed to provide a visual reference of the desired results of calibrating the sense amplifiers such that the resulting UT transmitted $X_p$, $Y_p$, and $Z_p$ EGM lead vectors can be visually compared with the displayed $X_E$, $Y_E$, and $Z_E$ external ECG vectors In step S100, illustrated in FIG. 8, the $X_E$, $Y_E$, and $Z_E$ external ECG vectors in the frontal X,Y plane, the transverse X,Z plane, and the sagittal Y,Z plane are optionally measured through switch array 66 that is coupled to the resistor network 90 of FIG. 6.

The $X_E$, $Y_E$, and $Z_E$ external lead vectors are developed through the skin electrodes and resistor network 90, amplified by the sense amplifiers 70, 72 and 74, respectively, of sense amplifier array 68, and provided to the logic and control circuitry 60 for display on display 62 in the manner depicted in FIG. 2. The vector values of each external xyz-vector and planar $X_E$, $Y_E$, and $Z_E$ external lead vectors over time are maintained in memory within the logic and control 60 of the external programmer 30. The external xyz-vector can also be developed and displayed by programmer 30.

Figure 9:
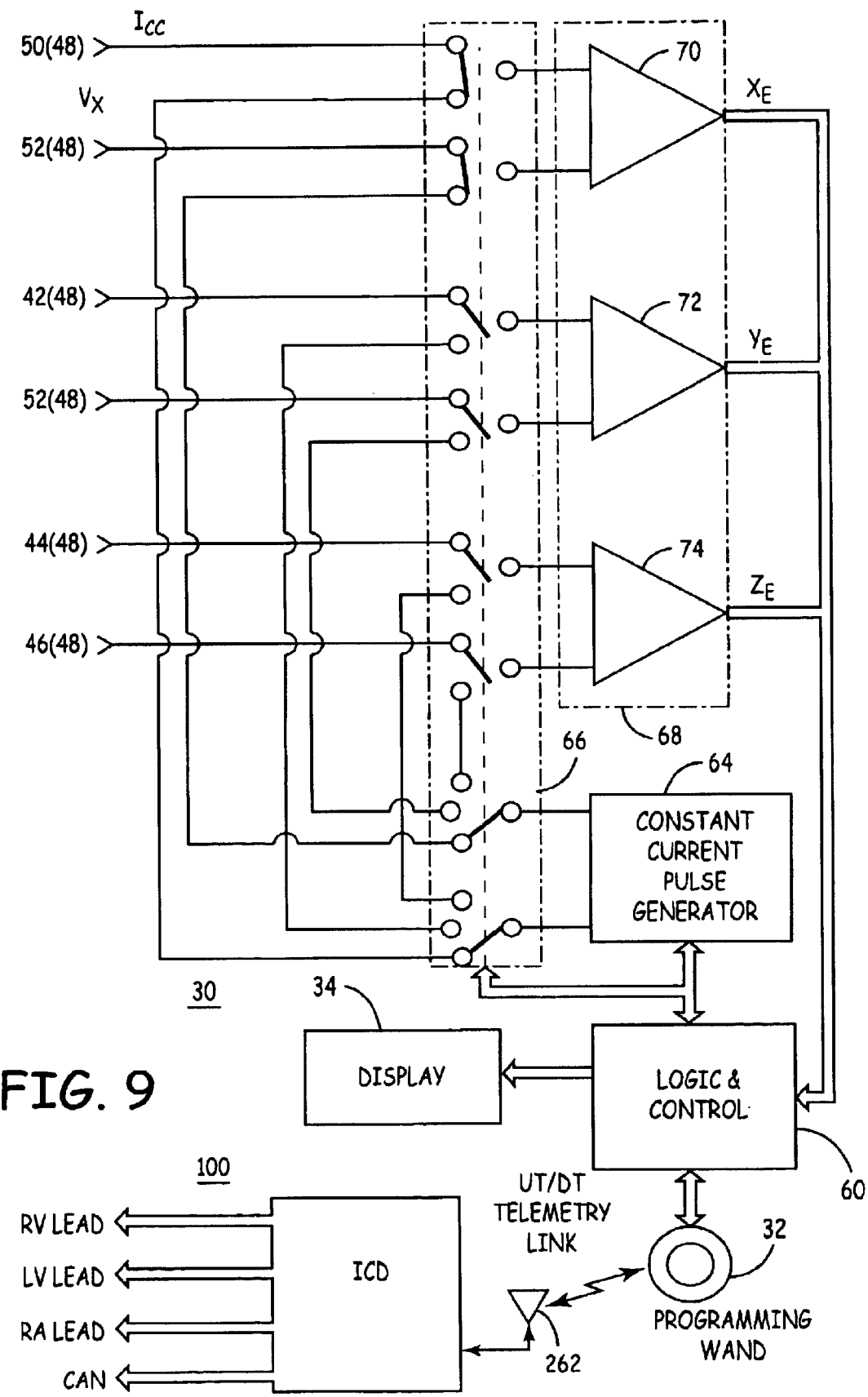
FIG. 9 is a circuit diagram illustrating the delivery of a constant current pulse signal to the right and left side terminals of the Frank resistor network of FIG. 6 to develop a voltage signal $V_x$ traversing the body that is detected by one or more selected electrode pair defining the lead vectors of FIG. 4 and uplink telemetry transmitted to the external programmer as the $X_P$ lead vector to develop a gain factor that the ICD sense amplifier sensing the $X_P$ lead vector is programmed to in steps of the calibration algorithm of FIG. 7A.
Figure 10:
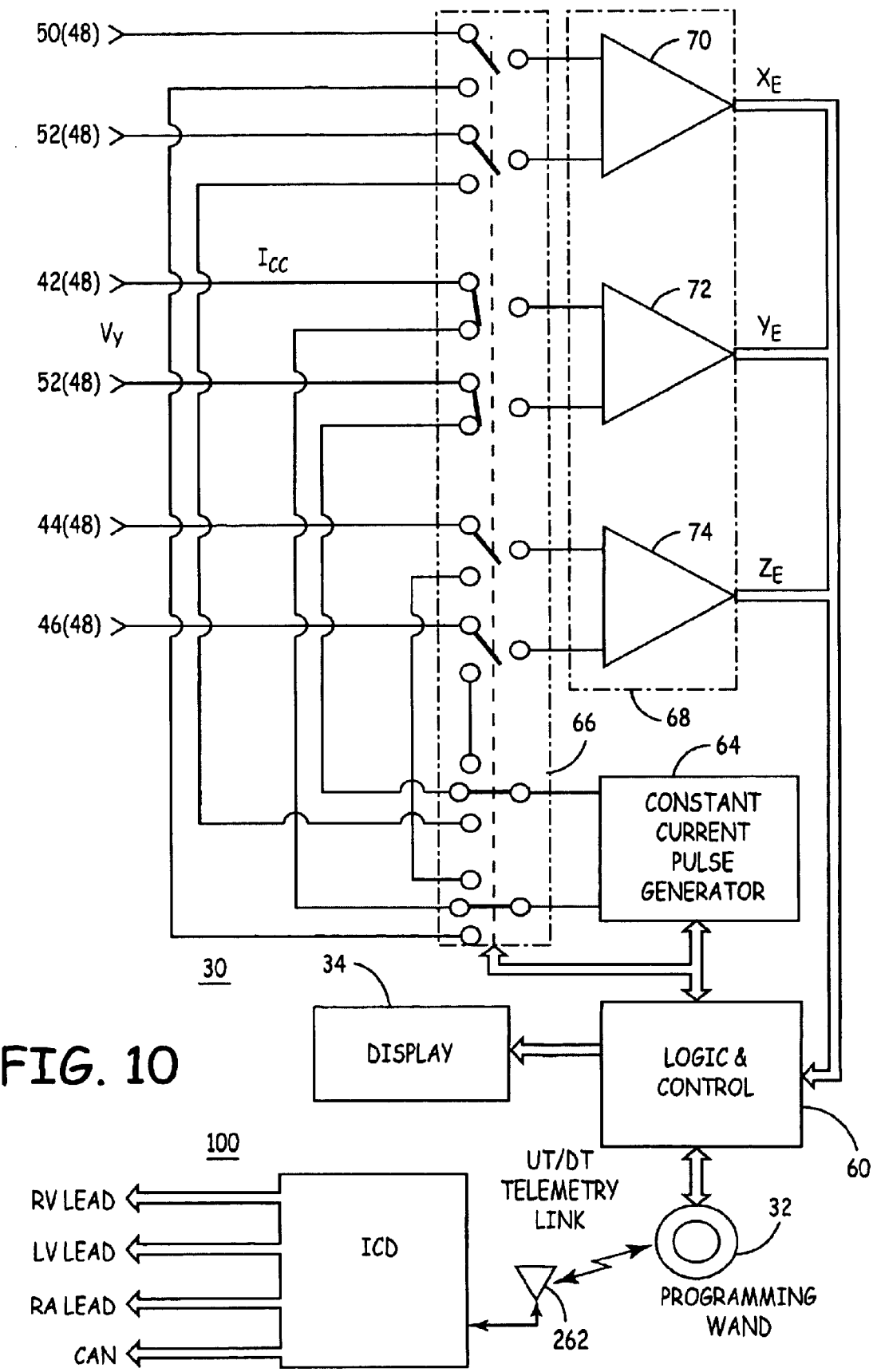
FIG. 10 is a circuit diagram illustrating the delivery of a constant current pulse signal to the cranial and caudal terminals of the Frank resistor network of FIG. 6, via external skin ECG electrodes to develop a voltage signal $V_Y$ traversing the body that is detected by one or more selected electrode pair defining the lead vectors of FIG. 4 and uplink telemetry transmitted to the external programmer as the $Y_P$ lead vector to develop a gain factor that the ICD sense amplifier sensing the $Y_P$ lead vector is programmed to in steps of the calibration algorithm of FIG. 7B.
Figure 11:
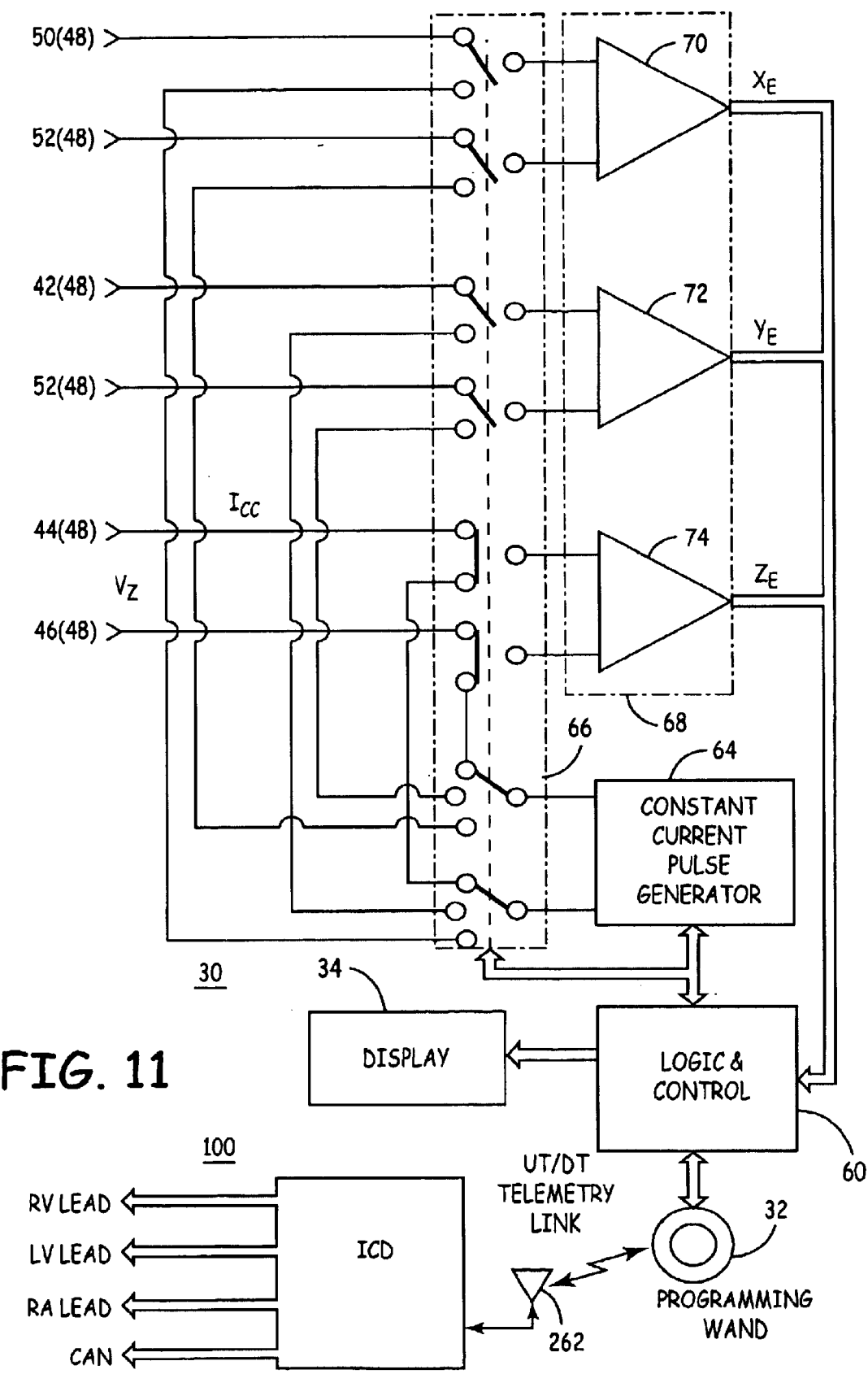
FIG. 11 is a circuit diagram illustrating the delivery of a constant current pulse signal to the ventral and dorsal terminals of the Frank resistor network of FIG. 6 via external skin ECG electrodes to develop a voltage signal $V_Z$ traversing the body that is detected by one or more selected electrode pair defining the lead vectors of FIG. 4 and uplink telemetry transmitted to the external programmer as the $Z_P$ lead vector to develop a gain factor that the ICD sense amplifier sensing the $Z_P$ lead vector is programmed to in steps of the calibration algorithm of FIG. 7C.

Steps S102 through S120 are then performed to develop and program the ICD sense amplifier sensing the $X_P$ lead vector across a programmed pair of implanted electrodes that define the lead vectors V1, V2, V3, V4, and V5. In step S102, the switches of the switch array 66 are set as shown in FIG. 9, and the ICD is commanded via a DT transmitted command to couple the ICD sense amplifier in sense amplifier array 270 to sense the $X_P$ lead vector across a programmed pair of implanted electrodes that define the lead vectors V1, V2, V3, V4, and V5. In step S106, a constant current pulse signal $I_{CC}$ is then delivered by constant current pulse generator 64 to the through closed switches of switch array 66 as shown in FIG. 9, and through the resistor network 90 to the skin electrodes.

In step S108, the ICD IPG 100 measures the $X_P$ lead vector across a programmed pair of implanted electrodes that define the lead vectors V1, V2, V3, V4, and V5. In step S110, the measured $X_P$ lead vector is UT transmitted to the programmer and displayed on display 34 by logic and control 60. The measured $X_P$ lead vector is characterized by a voltage $V_{XP}$.

A gain factor $G_X$ for the sense amplifier measuring the $X_P$ lead vector is then determined in step S112 from the formula $G_X=V_{XP}/I_{CC}$.

The gain for the sense amplifier measuring the $X_P$ lead vector is then programmed in a DT transmission to the ICD IPG in step S114, and performance of the programmed sense amplifier measuring the $X_P$ lead vector is then assessed in step S116. Switch array 66 can be returned to the configuration depicted in FIG. 8 and step S100 can be simultaneously performed to simultaneously view the $X_E$ lead vector and the $X_P$ lead vector on a split screen display. The user can also incrementally increase or decrease the gain factor for the sense amplifier measuring the $X_P$ lead vector to visually optimize the displayed $X_P$ lead vector.

The derivation of the gain factor and programming of the gain of the sense amplifier measuring the $Y_P$ lead vector is then conducted in steps S118–S132 of FIG. 7B. In step S118, the switch array 66 is set to the configuration of FIG. 10. The ICD is commanded to measure the $Y_P$ lead vector across an electrode pair defining the programmed one of the vectors V1, V2, V3, V4, & V5 in step S120. The constant current pulse signal $I_{CC}$ is delivered through the resistor network 90 of FIG. 6 to develop a voltage signal $V_Y$ traversing the body 10 in step S122. The $Y_P$ lead vector is measured in step S124 and UT transmitted to the programmer and displayed in step S126. The measured $Y_P$ lead vector is characterized by a voltage $V_{YP}$, and a gain factor $G_Y$ for the sense amplifier measuring the $Y_P$ lead vector is then determined from the formula $G_Y=V_{YP}/I_{CC}$ in step S128.

The gain for the sense amplifier measuring the $Y_P$ lead vector is then programmed in a DT transmission to the ICD IPG in step S130, and the performance of the programmed sense amplifier measuring the $Y_P$ lead vector is then assessed in step S132. Switch array 66 can be returned to the configuration depicted in FIG. 8 and step S100 can be simultaneously performed to simultaneously view the $Y_E$ lead vector and the $Y_P$ lead vector on a split screen display. The user can also incrementally increase or decrease the gain factor for the sense amplifier measuring the $Y_P$ lead vector to visually optimize the displayed $Y_P$ lead vector.

The derivation of the gain factor and programming of the gain of the sense amplifier measuring the $Z_P$ lead vector is then conducted in steps S134–S148 of FIG. 7B. In step S134, the switch array 66 is set to the configuration of FIG. 11. The ICD is commanded to measure the $Z_P$ lead vector across an electrode pair defining the programmed one of the vectors V1, V2, V3, V4, & V5 in step S136. The constant current pulse signal $I_{CC}$ is delivered through the resistor network 90 of FIG. 6 to develop a voltage signal $V_Z$ traversing the body 10 in step S138. The $Z_P$ lead vector is measured in step S140 and UT transmitted to the programmer and displayed in step S142. The measured $Z_P$ lead vector is characterized by a voltage $V_{ZP}$, and a gain factor $G_Z$ for the sense amplifier measuring the $Z_P$ lead vector is then determined from the formula $G_Z=V_{ZP}/I_{CC}$ in step S144.

The gain for the sense amplifier measuring the $Z_P$ lead vector is then programmed in a DT transmission to the ICD IPG in step S146, and the performance of the programmed sense amplifier measuring the $Z_P$ lead vector is then assessed in step S148. Switch array 66 can be returned to the configuration depicted in FIG. 8 and step S100 can be simultaneously performed to simultaneously view the $Z_E$ lead vector and the $Z_P$ lead vector on a split screen display. The user can also incrementally increase or decrease the gain factor for the sense amplifier measuring the $Z_P$ lead vector to visually optimize the displayed $Z_P$ lead vector.

Thus, the gains of the sense amplifiers of the sense amplifier array 270 can be calibrated to provide scaled representations of all three of the planar EGM vectors that can be combined into an xyz-vector or otherwise processed in VCG calculator block 272 and stored in RAM 226 or UT transmitted via telemetry I/O transceiver 260 to the external programmer 30.

Figure 12:
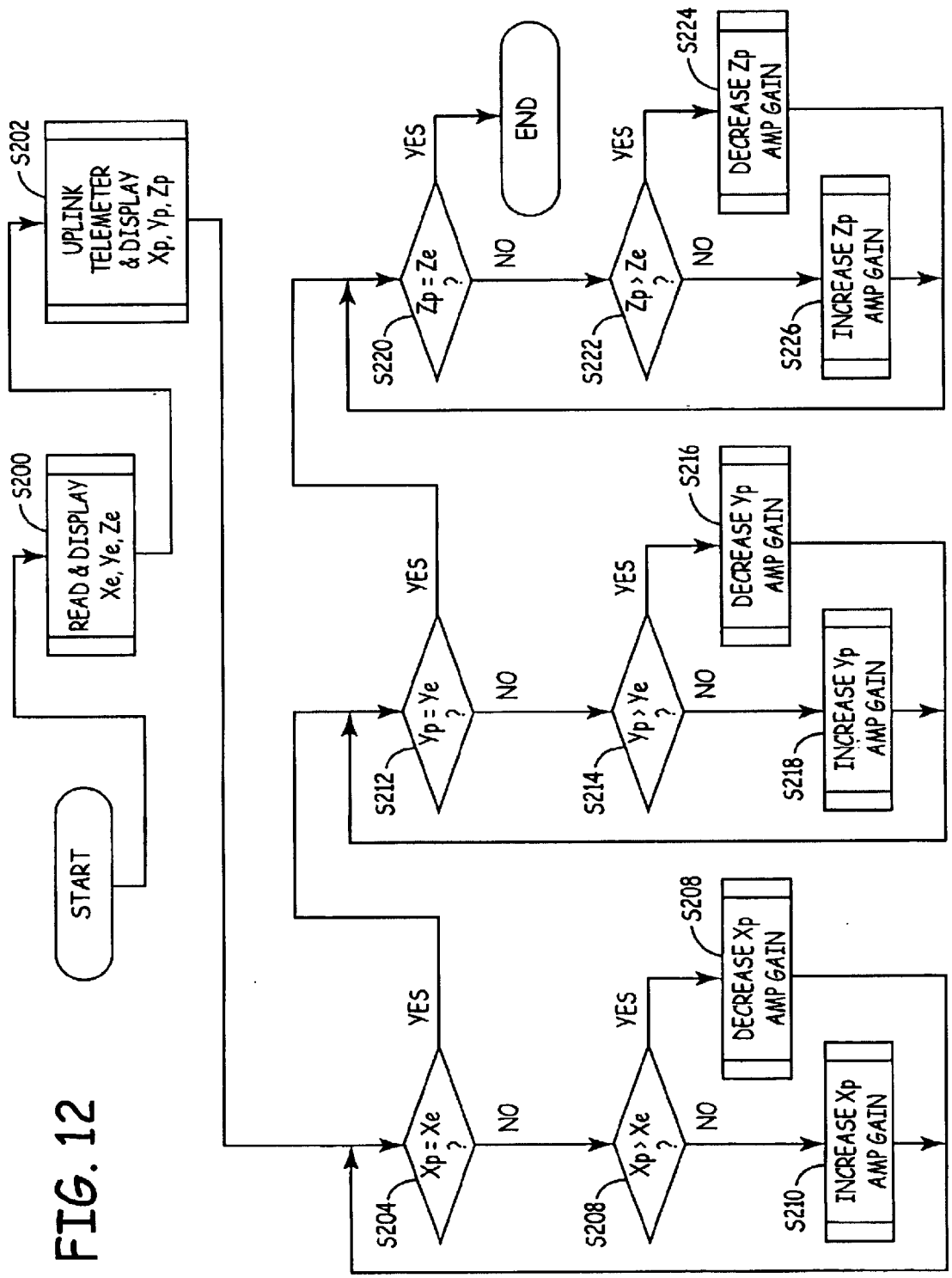
FIG. 12 is a flow chart illustrating the steps of an alternative calibration algorithm undertaken to correct the gain of each ICD sense amplifier that collectively develop the $X_P$, $Y_P$, and $Z_P$ planar vectors in the frontal X,Y plane, the transverse X,Z plane, and the sagittal Y,Z plane.

FIG. 12 illustrates an alternative method of deriving the gain factors for the sense amplifiers of the sense amplifiers block 270. In step S200, also illustrated in FIG. 8, the $X_E$, $Y_E$, and $Z_E$ external ECG vectors in the frontal X,Y plane, the transverse X,Z plane, and the sagittal Y,Z plane are measured through switch array 66 that is coupled to the resistor network 90 of FIG. 6. The $X_P$ lead vector, the $Y_P$ lead vector and the $Z_P$ lead vector are UT transmitted to the programmer 30 and displayed in step S202. The steps S204 through S210, S212 through S218 and S220 through S226 can be conducted in serial or parallel processing.

In steps S204–S210, the $X_P$ lead vector is compared with the $X_E$ lead vector to derive the instantaneous difference, and the gain of the selected EGM sense amplifier is adjusted via DT transmitted gain adjustment commands from the programmer 30 until the difference is minimized.

Similarly, in steps S212–S218, the $Y_P$ lead vector is compared with the $Y_E$ lead vector to derive the instantaneous difference, and the gain of the selected EGM sense amplifier is adjusted via DT transmitted gain adjustment commands from the programmer 30 until the difference is minimized.

Again, in steps S220–S226, the $Z_P$ lead vector is compared with the $Z_E$ lead vector to derive the instantaneous difference, and the gain of the selected EGM sense amplifier is adjusted via DT transmitted gain adjustment commands from the programmer 30 until the difference is minimized.

It should be noted that the gain factors derived in the above-described calibration processes can be employed to set the gains of the VCG sense amplifiers in sense amplifier array 270 as described above. Alternatively, the gain factors could be stored in RAM and employed to adjust the measured sets of data points of the $X_P$-vector VCG $Y_P$-vector VCG and $Z_P$-vector VCG.

Figure 13A:
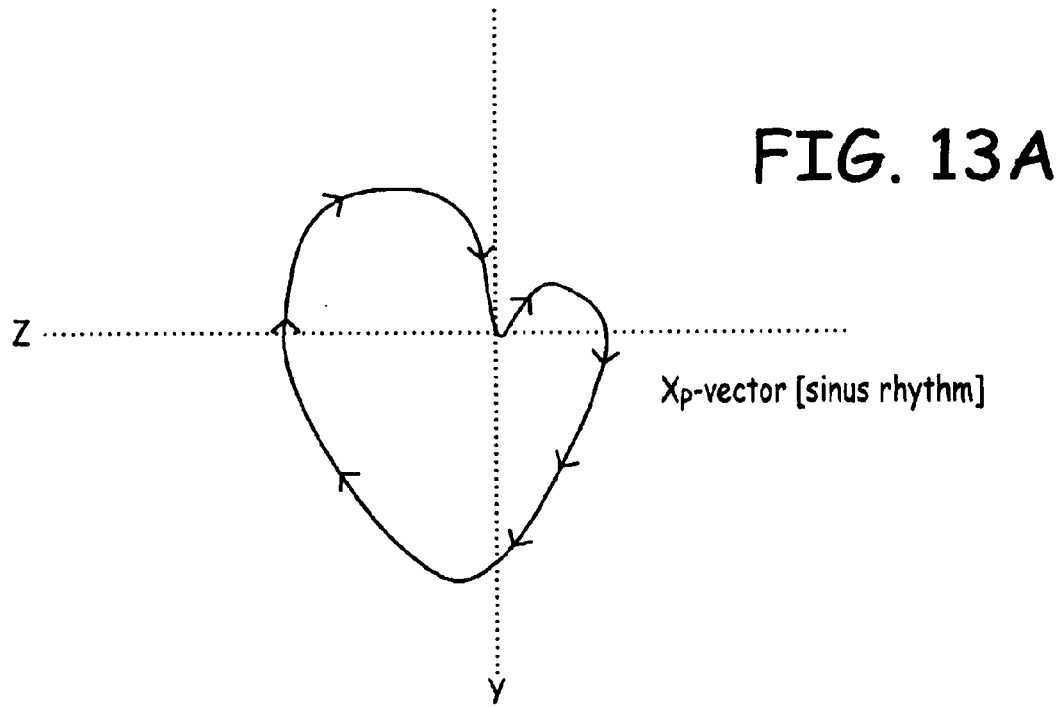
FIGS. 13A–13C depict the $X_P$-vector VCG of the combined P-wave and QRS wave projected in the right sagittal (Y,Z) plane of a patient's heart that exhibits normal sinus rhythm and episodes of WPW syndrome as well as ventricular tachycardia.
Figure 13B:
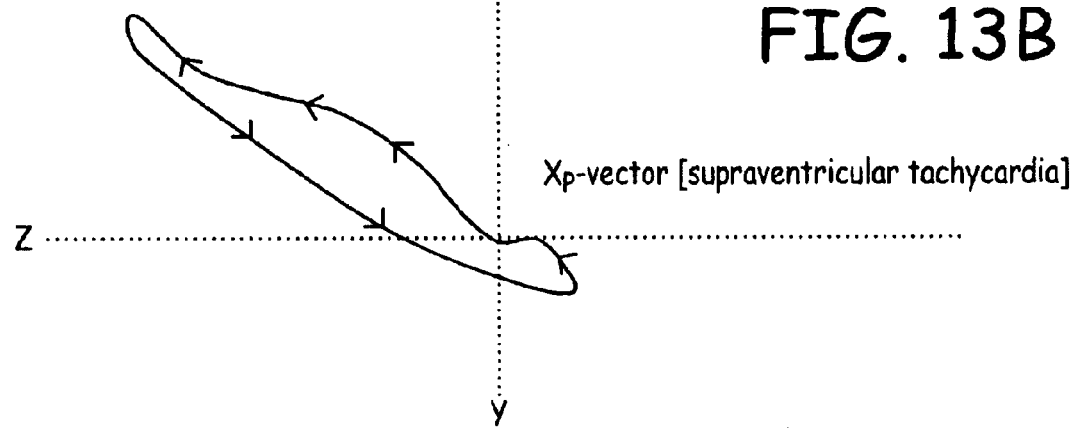
Figure 13C:
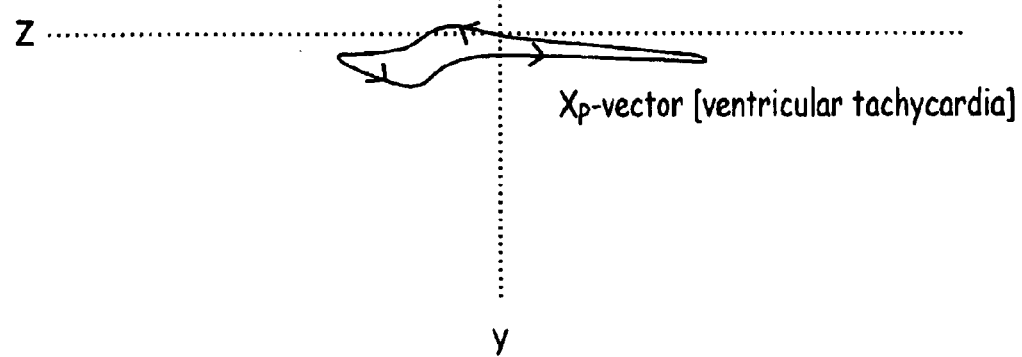

FIGS. 13A–13C depict the $X_P$-vector VCG of the combined P-wave and QRS wave projected in the right sagittal (Y,Z) plane of a patient's heart that exhibits episodes of WPW syndrome as well as the ventricular tachycardia. The $X_P$-vector VCG is calibrated in accordance with the present invention to be equivalent to the $X_E$-vector VCG that would be developed across the skin electrodes 44 and 46 through the resistor network of FIG. 6. The tracings of FIGS. 13A–13C mark the progression of the electrical wave front including its change in magnitude and direction through the atria (the P-wave) and the ventricles (the QRS wave) away from and back to the quiescent junction of the Y-axis and Z-axis over the PQRS time duration. For simplicity, the wave front of the T-wave loop is not illustrated in the tracings of FIGS. 13A–13C. The T-wave loop normally defines a smaller loop within the PQRS loop of FIG. 13A and is distorted when the heart is abnormal or is functioning abnormally.

FIG. 13A depicts the as an $X_P$-vector VCG that is developed within the IMD during normal function of the heart in sinus rhythm. FIG. 13B depicts the $X_P$-vector VCG of the heart that is developed within the IMD during pre-excitation in supraventricular tachycardia. FIG. 13C depicts the $X_P$-vector VCG of the heart that is developed within the IMD during ventricular tachycardia causing a bundle branch block (BBB). Obviously, the three loops are very different, and supraventricular and ventricular tachycardia with BBB episodes of FIGS. 13B and 13C could be easily discriminated from the normal sinus rhythm of FIG. 13A.

For example, the $X_P$-vector could be detected along the selected internal lead vector and stored in RAM for later UT transmission to the external programmer. The recording could be instigated by the patient during symptomatic episodes or automatically, when other detection criteria are satisfied and a therapy delivery is triggered. The episode data would be reproduced and displayed as tracings of FIGS. 13B and 13C upon the display screen of the programmer. The medical care provider observing the tracings can diagnose the abnormal function of the heart and change or prescribe a therapy, including a therapy delivered by the IMD to the patient's heart when detection criteria are met.

In accordance with a further aspect of the present invention, the detection and discrimination between various tachyarrhythmias and identification of false declarations of tachyarrhythmia can be made more robust and can have greater specificity among tachyarrhythmias of various types so that an appropriate therapy can be delivered. As described further below, the present invention provides for the derivation of vector magnitude and orientation data (as polar coordinates, for example), of high rate PQRST electrogram segments of heart cycles. The polar coordinate data can be mathematically plotted over the time of occurrence of the sensed PQRST electrogram as at least one of an x-axis vector projected into the reference sagittal plane as a sagittal VCG, a y-axis vector projected into the reference horizontal plane as a horizontal VCG, a z-axis vector projected into the reference frontal plane as a frontal VCG, and an xyz-vector in 3-D space. The loops plotted by each of the vectors can also be derived.

The derived maximum vector magnitude and orientation is representative of a particular heart rhythm. Similarly, the average axis vector magnitude and orientation (direction away from the origin) can be derived and is representative of a particular heart rhythm. The loop shape and loop area are also representative of a particular heart rhythm. Thresholding and template matching techniques can be employed to determine that a currently derived one or more of the maximum vector magnitude and orientation, average axis vector magnitude and orientation, loop shape, and loop area likely represents a particular heart rhythm.

For example, the present invention provides a way to distinguish oversensing of high amplitude T-waves across the RV sense electrodes, such as occur in Brugada—Brugada syndrome, as VSENSE events from an actual malignant ventricular tachyarrhythmia. The present invention develops the mean VCG vector and detects the T-wave peak in the T-wave loop. Brugada—Brugada syndrome is a disease limited to the anatomical region of the right ventricle. The T-wave loop within the VCG is predominantly developed by the left ventricle, and therefore it is always much smaller than the QRS loop even in Brugada—Brugada syndrome. Detection of QRS and T-wave vectors within the VCG loops simultaneously with the IEGM prevents the double counting of elevated T-waves along with the immediately preceding R-wave and consequent false positive detection of a high heart rate.

As described above, the $X_P$-vector VCGs of FIGS. 13A–13C are calibrated to the external $X_E$-vector VCGs, and the data points can be processed to develop reference templates for normal and abnormal heart conditions. The templates can be stored in IMD memory for use as primary or secondary detection criteria for detecting and identifying any subsequent episode of an arrhythmia that occurs. As primary detection criteria, the templates of supraventricular and ventricular tachycardia with BBB episodes of FIGS. 13B and 13C can be used to distinguish one from the other and from normal sinus rhythm. As secondary detection criteria, the tachyarrhythmia detection criteria can be defined to include conventional rate, regularity, onset, and rule-based detection criteria that are employed to distinguish various tachyarrhythmias. The templates of supraventricular and ventricular tachycardia with BBB episodes of FIGS. 13B and 13C can be used to distinguish one from the other when other detection criteria are unable to do so.

Figure 14A:
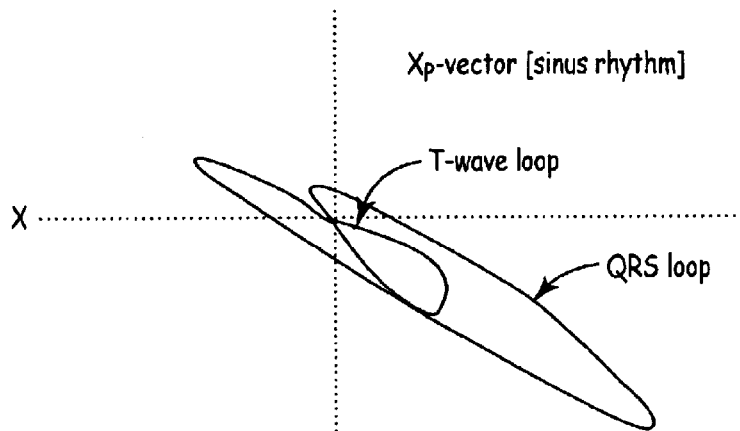
FIGS. 14A and 14B depict the $Z_P$-vector VCG of the T-wave loop within the PQRS loop in normal sinus rhythm and during an episode of ventricular tachycardia.
Figure 14B:
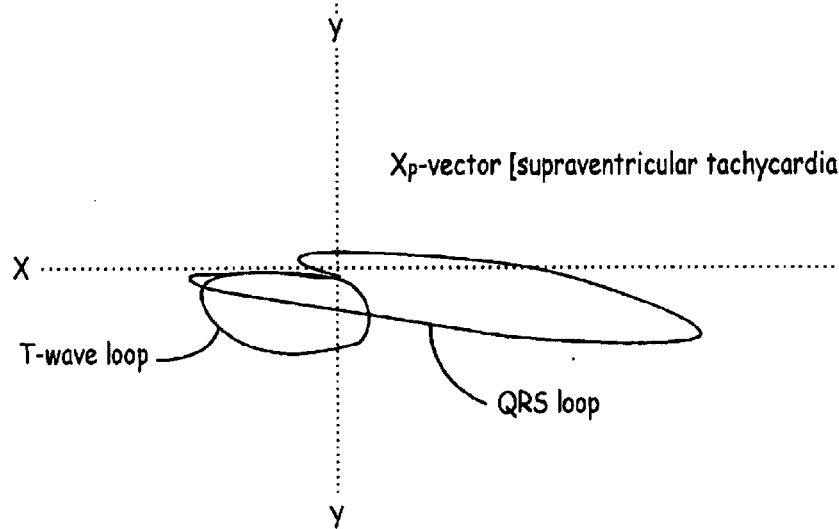

Similarly, FIGS. 14A and 14B depict the $Z_P$-vector VCG of the combined P-wave and QRS wave and the T-wave projected in the frontal (X,Y) plane of a patient's heart that exhibits the Brugada—Brugada syndrome. The $Z_P$-vector VCG is calibrated in accordance with the present invention to be equivalent to the $Z_E$-vector VCG that would be developed across the skin electrodes 50 and 52 through the resistor network of FIG. 6. The tracings of FIGS. 14A–14B mark the progression of the electrical wave front including its change in magnitude and direction through the atria (the P-wave) and the ventricles (the QRS wave) away from and back to the quiescent junction of the Y-axis and Z-axis over the PQRS time duration. In addition, the repolarization wave front of the T-wave loop is illustrated in the tracings of FIGS. 14A–14B.

During normal sinus rhythm, the T-wave loop of the heart exhibiting the Brugada—Brugada syndrome normally defines a smaller loop within the PQRS loop as shown in FIG. 14A. The T-wave loop can be highly is distorted when the heart is abnormal or is functioning abnormally in a way that can be used to identify the abnormality. Thus, the T-wave loop is distorted when the heart is in an episode of ventricular tachycardia as shown in FIG. 14B. This characteristic distortion can be employed as described above with reference to FIGS. 13A–13C to identify episodes of ventricular tachycardia occurring in a heart that exhibits the Brugada—Brugada syndrome.

This area distinguishing technique can be employed for each of the $X_P$-vector, $Y_P$-vector and $Z_P$-vector or for the composite xyz-vector to distinguish various tachyarrhythmias from normal sinus rhythm.

Figure 15:
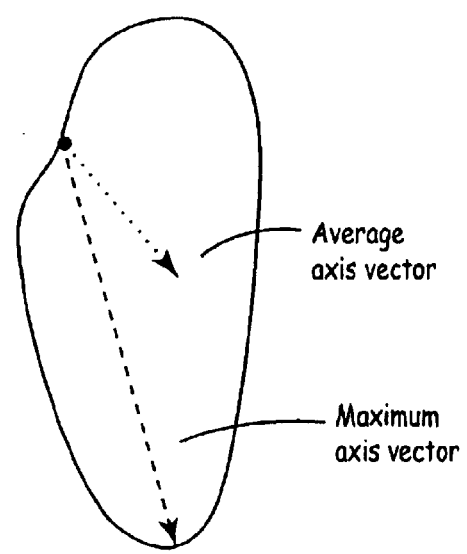
FIG. 15 is an exemplary VCG tracing that illustrates the relationship of an average axis vector derived from the full VCG tracing.

FIG. 15 shows one of the $X_P$-vector, $Y_P$-vector and $Z_P$-vector or the composite xyz-vector forming the VCG loop that is traced by the of each sampled vector, an instantaneous maximum amplitude vector (dashed line), and a calculated average axis vector (dotted line). The complete VCG loop is comprised of the polar coordinates of all of the vectors that are developed at the sampling frequency that is employed. In order to simplify the VCG analysis, the average (or mean) axis vector, that is the average or all magnitudes and angular deviations of the instantaneous vector over the duration of the QRS wave or T-wave, could be determined for every single beat. The average axis vector of the QRS wave or T-wave has a characteristic magnitude and angle of orientation from the origin for normal sinus rhythm and for the various forms of tachyarrhythmias or other arrhythmias. The average axis vector for each of the $X_P$-vector, $Y_P$-vector and $Z_P$-vector of the QRS wave or T-wave can be determined. Then, it is possible to distinguish one rhythm from another by comparing the calculated average axis vector to known or reference average axis vectors that can be determined and stored in memory in a patient work-up. The accuracy of the rhythm interpretation would be extremely high if the average axis vector is calculated for all of the $X_P$-vector, $Y_P$-vector and $Z_P$-vector and comparisons are made to the respective reference average axis $X_P$-vector, $Y_P$-vector and $Z_P$-vector.

Computation of the 3-D xyz-vector engages much more processing power than the computation of the single plane, 2-D vectors. Accordingly, use of the high processing power to derive the xyz-vector and consequent higher accuracy of the analysis might be made programmable for specific patients where it proves to be of benefit.

Figure 16:
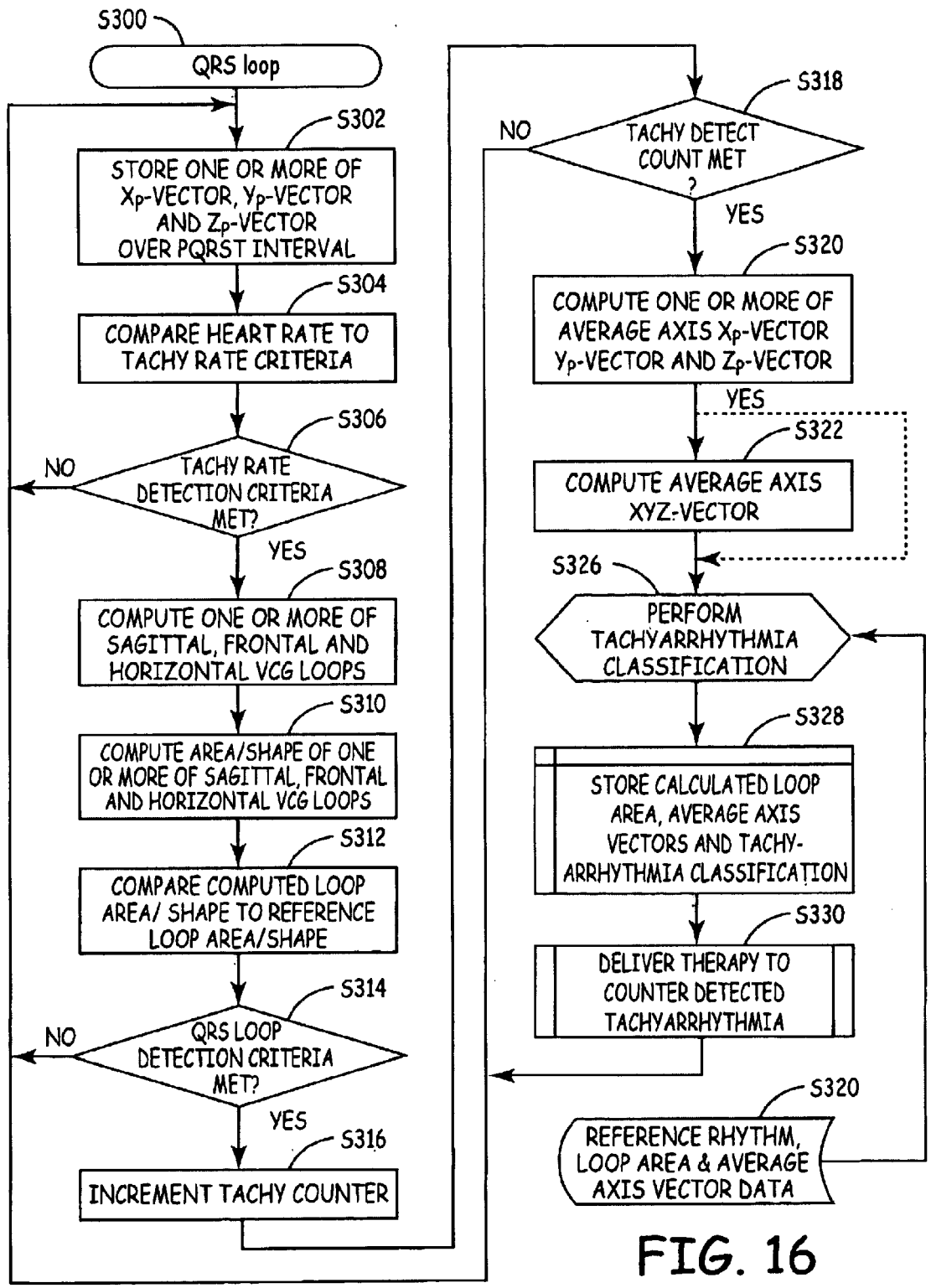
FIG. 16 is a flow chart illustrating an exemplary algorithm for employing sagittal, frontal and horizontal VCG and/or the xyz-vector VCG developed by the IMD to augment the use of rate-based tachyarrhythmia detection criteria to distinguish between a true ventricular tachyarrhythmia and an apparent ventricular tachyarrhythmia declared due to detection of high amplitude T-waves as ventricular sense events.

FIG. 16 illustrates an exemplary flow chart of a tachyarrhythmia discrimination process employing one or more of the $X_P$-vector, $Y_P$-vector, $Z_P$-vector and xyz-vector and comparisons made to respective ones of the reference area and average axis $X_P$-vector, $Y_P$-vector, $Z_P$-vector and xyz-vector. The algorithm of FIG. 16 is preferably embodied in an IMD, e.g., an ICD of the type shown in FIG. 5, particularly for detecting and discriminating particular ventricular and supraventricular tachyarrhythmias of the types described above and applying the appropriate anti-tachyarrhythmia therapy. In particular, the algorithm of FIG. 16 discriminates between apparent, but falsely declared, ventricular tachyarrhythmias that provisionally satisfy conventional tachycardia detection criteria, notably high rate, and true ventricular tachycardias. Such false declarations can occur in certain hearts because of high amplitude T-waves that are incorrectly detected as R-waves whereby each QRST complex is detected as two VSENSE events.

In step S302, the selected one or more of the $X_P$-vector, $Y_P$-vector and $Z_P$-vector of the selected one or more of the P-wave, QRS wave or T-wave are derived and stored during each heart cycle. In other words, the magnitude and orientation of each sampled EGM signal along the selected ones of the V1, V2, V3, V4, V5 lead vectors developed by the gain corrected vector amplifiers in lead amplifiers block 270 of FIG. 5 is temporarily stored in RAM 226 as sample time related, polar coordinate values. Thus, a set of data points are developed and temporarily stored. The storage may be on a FIFO basis typically over at least two heart cycles.

Each stored data set would ordinarily be accompanied in real time by a VSENSE event generated by the R-wave sense amplifier 200 when the R-wave amplitude exceeds a sense threshold. However, high amplitude T-waves could also exceed the ventricular sense threshold and be erroneously identified as an R-wave. The interval between the current VSENSE event and the preceding VSENSE event is simultaneously measured and compared to a tachycardia rate threshold in step S304, and a short interval between such a high amplitude T-wave and the succeeding R-wave or an R-wave and the T-wave in the same heart cycle could satisfy the tachycardia rate threshold.

If the tachycardia rate threshold is met, then the two data sets stored in step S302 are processed by the VCG calculator block 272 of FIG. 5 in steps S308 and S310 to compute the area and/or shape of each VCG loop to ascertain whether the two apparent R-waves are true R-waves or not. As noted above, the T-wave VCG loop differs in shape and area from the R-wave VCG loop, and so the computed VCG loops are compared to the stored thresholds or loop templates in step S314 for true R-waves. If the VCG loop shape and/or area satisfy the QRS loop area and/or shape templates, then a true R-wave is declared in step S316, and a tachycardia count is incremented in step S318. If the computed loop shape or area does not satisfy the reference QRS loop shape or area, then the ventricular sense event is declared to be a T-wave, and the process of steps S302–S314 is repeated. In this way, steps S302–S316 provide an enhanced discrimination function for verifying true R-waves and not incrementing the tachycardia count when the apparent high rate heart cycle is erroneously based on a high amplitude T-wave starting or ending the heart cycle.

The tachycardia counter is typically a FIFO counter that maintains a running count of the number of high rate (short interval) heart cycles that have been counted in a programmed number of past heart cycles, e.g., 32 or 54 preceding heart cycles. Typically, ventricular tachyarrhythmia detection is effected by incrementing the tachycardia count on each high rate R-wave and decrementing the tachycardia count on low rate R-wave. The count of the tachycardia counter is compared to a tachycardia threshold to declare a tachycardia when a programmed number of successive high rate R-waves exceed the tachycardia threshold. At the same time the count of the tachycardia counter is compared to other tachyarrhythmia thresholds, e.g., a ventricular fibrillation threshold that can be satisfied when a programmed fraction of the programmed number of total heart cycles are high rate heart cycles. Generally, the first count threshold to be satisfied causes a provisional declaration of the corresponding tachycardia or tachyarrhythmia. But, other criteria, e.g., the suddenness of onset, the rate stability, and other rule-based criteria are applied in the attempt to ascertain the specific type of tachyarrhythmia is occurring and discriminate it from other closely resemble tachyarrhythmias. Anti-tachyarrhythmia therapies are tailored to very specific arrhythmias, and it is highly important to trigger delivery of the appropriate anti-tachyarrhythmia therapy and not deliver an inappropriate anti-tachyarrhythmia. Steps S320–S326 can be employed with such prior discrimination systems enhance the specificity of the discrimination between various types of tachyarrhythmias that might be declared when the tachycardia detect count is met in step S318.

When a tachycardia count threshold is met in step S318, then the algorithm discriminates between types of tachyarrhythmias as a function of the average axis vector depicted in FIG. 15 and described above so that an appropriate programmed anti-tachyarrhythmia therapy can be delivered in step S330. In step S320, one or more or all of the average axis $X_P$-vector, $Y_P$-vector and $Z_P$-vector (FIG. 15), is computed. The average axis xyz-vector can be computed in step S322 if all three of the average axis $X_P$-vector, $Y_P$-vector and $Z_P$-vector are computed in step S320 or step S322 can be programmed OFF. Classification of the tachyarrhythmia is conducted in step S326 employing stored reference cardiac rhythm and average axis vector data retrieved in S324 that are compared to the prevailing rhythm and the average axis xyz-vector determined in step S322 or the one or more of the average axis $X_P$-vector, $Y_P$-vector and $Z_P$-vector determined in step S318.

The determined tachyarrhythmia identification and the associated data are stored in RAM in the ICD IPG in step S328 for UT transmission and analysis at a later time. The appropriate therapy is then delivered in step S330.

All patents and publications referenced herein are hereby incorporated by reference in there entireties.

It will be understood that certain of the above-described structures, functions and operations of the systems of the preferred embodiments are not necessary to practice the present invention and are included in the description simply for completeness of an exemplary embodiment or embodiments. It will also be understood that there may be other structures, functions and operations ancillary to the typical operation of an anti-tachyarrhythmia control device that are not disclosed and are not necessary to the practice of the present invention. In addition, it will be understood that specifically described structures, functions and operations set forth in the above-incorporated patents and publications can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A method of developing a vectorcardiogram projected onto at least one of reference sagittal, horizontal, and frontal planes of the body employing an implantable medical device comprising:

implanting a pair of vectorcardiogram sense electrodes to define an internal lead vector in the body having a vector orientation in relation to the reference sagittal, horizontal, and frontal planes of the body;

coupling the pair of vectorcardiogram sense electrodes with the implantable medical device;

sensing the PQRST electrogram of the heart across the internal lead vector; and deriving the orientation and magnitude of the wave front of at least one of the P-wave, QRS wave and T-wave of the sensed PQRST electrogram aver the fine of occurrence of the sensed PQRST electrogram as at least one of an x-axis vector projected into the reference sagittal plane as a sagittal vectorcardiogram, a y-axis vector projected into the reference horizontal plane as a horizontal vectorcardiogram, and a z-axis vector projected into the reference frontal plane as a frontal vectorcardiogram.

2. The method of claim 1, wherein the implanting step comprises implanting the pair of electrodes in selected locations within the right ventricle, the right atrium and the coronary sinus of the heart.

3. The method of claim 1, wherein the implanting step comprises implanting a first electrode of the pair of electrodes within one of the right ventricle, the right atrium and the coronary sinus of the heart and a second electrode of the pair of electrodes subcutaneously and remote from the heart.

4. The method of claim 1, further comprising the steps of:

deriving a gain factor that compensates for the angular deviation of the internal lead vector out of coplanar relation with the at least one of the reference sagittal, horizontal, and frontal planes of the body that the at least one of the sagittal vectorcardiogram, horizontal vectorcardiogram, and frontal vectorcardiogram is referenced to.

5. The method of claim 4, wherein the step of deriving a gain factor comprises:

delivering a known current to the patients' body in at least one of the reference signal, horizontal, and frontal planes of the body;

measuring the voltage induced by the delivered current across the internal lead vector in the body; and calculating the gain factor as the dividing the induced voltage by the known current.

6. The method of claim 4, wherein the step of deriving a gain factor comprises:

delivering a known current to the patients' body through a pair of skin electrodes in at least one of the reference sagittal, horizontal, and frontal planes of the body;

within the implantable medical device, measuring the voltage induced by the delivered current across the internal lead vector in the body;

uplink telemetry transmitting the measured voltage to an external medical device in telemetry communication with the internal medical device;

within the external medical device, calculating the gain factor by dividing the induced voltage by the known current; and downlink telemetry transmitting the calculated gain factor to the implantable medical device to be employed in the amplifying step.

7. The method of claim 4, wherein the step of deriving a gain factor comprises:

sensing the PQRST electrocardiogram of the heart across an external lead vector referenced to at least one of the reference sagittal, horizontal, and frontal planes of the body;

comparing the sensed PQRST electrocardiogram to the sensed PQRST electrogram to derive a difference between the sensed PQRST electrocardiogram to the sensed PQRST electrogram; and calculating a gain factor that reduces the difference substantially to zero.

8. The method of claim 4, wherein the step of deriving a gain factor comprises:

sensing the PQRST electrocardiogram of the heart across an external lead vector referenced to at least one of the reference sagittal, horizontal, and frontal planes of the body;

uplink telemetry transmitting the sensed PQRST electrogram to an external medical device;

comparing the sensed PQRST electrocardiogram to the sensed PQRST electrogram, to derive a difference between the sensed PQRST electrocardiogram to the sensed PQRST electrogram;

calculating a gain factor that reduces the difference substantially to zero; and downlink telemetry transmitting the calculated gain factor to the implantable medical device to be employed in the amplifying step.

9. The method of claim 1, further comprising the step of analyzing the one of the taxis vector, y-axis vector, and z-axis vector to ascertain the state of health of the heart.

10. The method of claim 1, further comprising the steps of:

analyzing the one of the x-axis vector, y-axis vector, and z-axis vector to ascertain the state of health of the heart; and delivering a therapy to a head exhibiting, through the analysis of the one of the x-axis vector, y-axis vector, and z-axis vector, an abnormal state of health.

11. A method of developing a vectorcardiogram projected onto at least one of reference sagittal, horizontal, and frontal planes of the body employing a cardiac implantable medical device comprising:

implanting a first pair of vectorcardiogram sense electrodes in the body to define a first internal lead vector having a first vector orientation in relation to the reference sagittal, horizontal, and frontal planes of the body;

coupling the first pair of vectorcardiogram sense electrodes to the implantable medical device;

sensing a first PQRST electrogram of the heart across the first internal lead vector;

implanting a second pair of vectorcardiogram sense electrodes in the body to define a second internal lead vector having a second vector orientation in relation to the reference sagittal, horizontal, and frontal planes of the body;

coupling the second pair of vectorcardiogram sense electrodes to the implantable medical device;

sensing a second PQRST electrogram of the heart across the second internal lead sector;

deriving the orientation and magnitude of the wave front of at least one of the P-wave, QRS wave and T-wave over the time of occurrence of the first sensed PQRST electrogram as a first one of an x-axis vector projected into the reference sagittal plane as a sagittal vectorcardiogram, a y-axis vector projected into the reference horizontal plane as a horizontal vectorcardiogram, and a z-axis vector projected into the reference frontal plane as a frontal vectorcardiogram; and deriving the orientation and magnitude of the wave front of at least one of the P-wave, QRS wave and T-wave over the time of occurrence of the second sensed PQRST electrogram as a second one of an x-axis vector projected into the reference sagittal plane as a sagittal vectorcardiogram, a y-axis vector projected into the reference horizontal plane as a horizontal vectorcardiogram, and a z-axis vector projected into the reference frontal plane as a frontal vectorcardiogram.

12. The method of claim 11, wherein:

the step of sensing the first PQRST electrogram further comprises:

deriving a first gain factor that compensates for the angular deviation of the first internal lead vector out of coplanar relation with the first one of the reference sagittal, horizontal, and frontal planes of the body that the first one of the sagittal vectorcardiogram, horizontal vectorcardiogram, and frontal vectorcardiogram is traced into; and amplifying the first sensed PQRST electrogram by the derived first gain factor; and the step of sensing the second PQRST electrogram further comprises:

deriving a second gain factor that compensates for the angular deviation of the second internal lead vector out of coplanar relation with the second one of the reference sagittal, horizontal, and frontal planes of the body that the second one of the sagittal vectorcardiogram, horizontal vectorcardiogram, and frontal vectorcardiogram is traced into; and amplifying the second sensed PQRST electrogram by the derived second gain factor.

13. The method of claim 11, wherein the implanting steps comprises implanting the first and second pairs of electrodes at selected locations within the right ventricle, the right atrium, and the coronary sinus of the heart.

14. The method of claim 11, wherein the implanting steps comprise implanting the first and second pair of electrodes at selected locations within the right ventricle, the right atrium, and the coronary sinus of the heart and subcutaneously and remote from the heart.

15. A method of developing an xyz-vectorcardiogram projected into three dimensional space in spatial reference to at least one of reference sagittal, horizontal, and frontal planes of the body employing an implantable medical device, comprising:

implanting a pair of vectorcardiogram sense electrodes in the body to define an internal lead vector having a vector orientation in relation to the reference sagittal, horizontal, and frontal planes of the body;

coupling the a pair of vectorcardiogram sense electrodes to the implantable medical device;

sensing the PQRST electrogram of the heart across the internal lead vector; and deriving the orientation and magnitude of the wave front of at least one of the P-wave, QRS wave and T-wave of the sensed PQRST electrogram over the time of occurrence of the sensed PQRST electrogram as an xyz-vectorcardiogram projected into three-dimensional space in reference to at least one of reference sagittal, horizontal, and frontal planes of the body.

16. The method of claim 15, further comprising the step of deriving the orientation and magnitude of the wave front of at least one of the P-wave, QRS wave and T-wave of the sensed PQRST electrogram over the time of occurrence of the sensed PQRST electrogram as at least one of an x-axis vector projected into the reference sagittal plane as a sagittal vectorcardiogram, a y-axis vector projected into the reference horizontal plane as a horizontal vectorcardiogram, and a z-axis vector projected into the reference frontal plane as a frontal vectorcardiogram.

17. The method of claim 16, wherein the sensing step further comprises:

deriving a gain factor that compensates for the angular deviation of the internal lead vector out of coplanar relation with the at least one of the reference sagittal, horizontal, and frontal planes of the body that the at least one of the sagittal vectorcardiogram, horizontal vectorcardiogram, and frontal vectorcardiogram is traced into; and amplifying the sensed PQRST electrogram by the derived gain factor.

18. The method of claim 15, wherein the sensing step further comprises:

deriving a gain factor that compensates for the angular deviation of the internal lead vector out of coplanar relation with the at least one of the reference sagittal, horizontal, and frontal planes of the body that the xyz-vectorcardiogram is misted to; and amplifying the sensed PQRST electrogram by the derived gain factor.

19. The method of claim 15, wherein the implanting step comprises implanting the pair of electrodes in selected locations within the right ventricle, the right atrium and the coronary sinus of the heart.

20. The method of claim 15, wherein the implanting step comprises implanting a first electrode of the pair of electrodes within one of the right ventricle, the right atrium and the coronary sinus of the heart and a second electrode; of the pair of electrodes subcutaneously and remote from the heart.

21. A cardiac implantable medical device that develops a vectorcardiogram projected onto at least one of reference sagittal, horizontal, and frontal planes of the body comprising:

a pair of vectorcardiogram sense electrodes adapted to be implanted in the body to define an internal lead vector having a vector orientation In relation to the reference sagittal, horizontal, and frontal planes of the body;

means for sensing the PQRST electrogram of the heart across the internal lead vector; and means for deriving the orientation and magnitude of the wave front of at least one of the P-wave; QRS wave and T-wave of the sensed PQRST electrogram over the time of occurrence of the sensed PQRST electrogram as at least one of an x-axis vector projected into: the reference sagittal plane as a sagittal vectorcardiogram, a y-axis vector projected into the reference horizontal plane as a horizontal vectorcardiogram, and a z-axis vector projected into the reference frontal plane as a frontal vectorcardiogram.

22. The implantable medical device of claim 21, wherein the pair of vectorcardiogram sense electrodes are at locations selected from the right ventricle, the right atrium and the coronary sinus of the heart.

23. The implantable medical device of claim 21, wherein the pair of vectorcardiogram sense electrodes comprises a first electrode within one of the right ventricle, the right atrium and the coronary sinus of the heart and a second electrode implanted subcutaneously and remote from the head.

24. The implantable medical device of claim 21, further comprising:

means for deriving a gain factor that compensates for the angular deviation of the internal lead vector out of coplanar relation with the at least one of the reference sagittal horizontal, and frontal planes of the body that the at least one of the sagittal vectorcardiogram, horizontal vectorcardiogram, and frontal vectorcardiogram is traced into; and wherein the sensing means further comprises:

means for amplifying the sensed PQRST electrogram by the derived gain factor.

25. The implantable medical device of claim 24, wherein the means for deriving a gain factor comprises:

means for delivering a known current to the patients' body in at least one of the reference sagittal, horizontal, and frontal planes of the body;

means for measuring the voltage induced by the delivered current across the internal lead vector in the body; and means for calculating the gain factor as the dividing the induced voltage by the known current.

26. The implantable medical device of claim 24, wherein the means for deriving a gain factor comprises:

means for delivering a known current to the patients' body through a pair of skin electrodes in at least one of the reference sagittal, horizontal, and frontal planes of the body;

means within the implantable medical device for measuring the voltage induced by the delivered current across the internal lead vector in the body;

means within the implantable medical device for uplink telemetry transmitting the measured voltage to an external medical device in telemetry communication with the internal medical device;

means within the external medical device for calculating the gain factor by dividing the induced voltage by the known current; and means within the external medical device for downlink telemetry transmitting the calculated gain factor to the implantable medical device to be employed in the amplifying step.

27. The implantable medical device of claim 24, wherein the means for deriving a gain factor comprises:

means for sensing the PQRST electrocardiogram of the heart across an external lead vector referenced to at least one of the reference sagittal, horizontal, and frontal planes of the body;

means for comparing the sensed PQRST electrocardiogram to the sensed PQRST electrogram to derive a difference between the sensed PQRST electrocardiogram to the sensed PQRST electrogram; and means for calculating a gain factor that reduces the difference substantially to zero.

28. The implantable medical device of claim 24, wherein the means for deriving a gain factor comprises:

means for sensing the PQRST electrocardiogram of the heart across an external lead vector referenced to at least one of the reference sagittal, horizontal, and frontal planes of the body;

means within the implantable medical device for uplink telemetry transmitting the sensed PQRST electrogram to an external medical device;

means within the external medical device for comparing the sensed PQRST electrocardiogram to the sensed PQRST electrogram to derive a difference between the sensed PQRST electrocardiogram to the sensed PQRST electrogram;

means within the external medical device for calculating a gain factor that reduces the difference substantially to zero; and means within the external medical device for downlink telemetry transmitting the calculated gain factor to the implantable medical device to be employed in the amplifying stop.

29. The implantable medical device of claim 21, further comprising means for analyzing the one of the x-axis vector, y-axis vector, and z-axis vector to ascertain the state of health of the heart.

30. The implantable medical device of claim 21, further comprising:

means for analyzing the one of the x-axis vector, y-axis vector, and z-axis vector to ascertain the state of health of the head; and means for delivering a therapy to a head exhibiting, through the analysis of the one of the x-axis vector, y-axis vector, and z-axis vector, an abnormal state of health.

31. A cardiac implantable medical device that develops a vectorcardiogram projected onto at least one of reference sagittal, horizontal, and frontal planes of the body comprising:

a first pair of vectorcardiogram sense electrodes adapted to be implanted within the body defining a first internal lead vector having a first vector orientation in relation to the reference sagittal, horizontal, and frontal planes of the body;

first sensing means for sensing a first PQRST electrogram of the heart across the first internal lead vector;

a second pair of vectorcardiogram sense electrodes adapted to be implanted within the body defining a second internal lead vector having a second vector orientation in relation to the reference sagittal, horizontal, and frontal planes of the body;

second sensing means for sensing a second PQRST electrogram of the heart across the second internal lead vector;

means for deriving the orientation and magnitude of the wave front of at least one of the P-wave, ORS wave and T-wave over the time of occurrence of the first sense PQRST electrogram a first one of an x-axis vector projected Into the reference sagittal plane as a sagittal vectorcardiogram, a y-axis vector projected into the reference horizontal plane as a horizontal vectorcardiogram, and a z-axis vector projected into the reference frontal plane as a frontal vectorcardiogram; and means for deriving the orientation and magnitude of the wave front of at least one of the P-wave, QRS wave and T-wave over the time of occurrence of the second sensed PQRST electrogram as a second one of an x-axis vector projected into the reference sagittal plane as a sagittal vectorcardiogram, a y-axis vector projected into the reference horizontal plane as a horizontal vectorcardiogram, and a z-axis vector projected into the reference frontal plane as a frontal vectorcardiogram.

32. The implantable medical device of claim 31, wherein:

the first sensing means further comprises:
  means for deriving a first gain factor that compensates for the angular deviation of the first internal lead vector out of coplanar relation with the first one of the reference sagittal, horizontal, and frontal planes of the body that the first one of the sagittal vectorcardiogram, horizontal vectorcardiogram, and frontal vectorcardiogram is traced into; and
  means for amplifying the first sensed PQRST electrogram by the derived first gain factor; and the second sensing means further comprises:
  deriving a second gain factor that compensates for the angular deviation of the second internal lead vector out of coplanar relation with the second one of the reference sagittal, horizontal, and frontal planes of the body that the second one of the sagittal vectorcardiogram, horizontal vectorcardiogram, and frontal vectorcardiogram is traced into; and
  amplifying the second sensed PQRST electrogram by the derived second gain factor.

33. The implantable medical device of claim 31, wherein the first and second pairs of electrodes are at selected locations of the right ventricle, the right atrium, and the coronary sinus of the heart.

34. The implantable medical device of claim 31, wherein the first and second pair of electrodes are at selected locations of the right ventricle, the right atrium, the coronary sinus of the heart, and subcutaneously and remote from the heart.

35. A cardiac implantable medical device that develops an xyz vectorcardiogram projected into three dimensional space in spatial reference to at least one of reference sagittal, horizontal, and frontal planes of the body comprising:

a pair of vectorcardiogram sense electrodes adapted to be implanted in the body to define an internal lead vector having a vector orientation in relation to the reference sagittal, horizontal, and frontal planes of the body;

means for sensing the PQRST electrogram of the heart across the internal lead vectors and means for deriving the orientation and magnitude of the wave front of at least one of the P-wave, QRS wave and T-wave of the sensed PQRST electrogram over the time of occurrence of the sensed PQRST electrogram as an xyz-vectoroardiogram projected into three dimensional space in reference to at least one of reference sagittal, horizontal, and frontal planes of the body.

36. The implantable medical device of claim 35, further comprising means for deriving the orientation and magnitude of the wave front of at least one of the P-wave, QRS wave and T-wave of the sensed PQRST electrogram over the time of occurrence of the sensed PQRST electrogram as at least one of an x-axis vector projected into the reference sagittal plane as a sagittal vectorcardiogram, a y-axis vector projected into the reference horizontal plane as a horizontal vectorcardiogram, and a z-axis vector projected into the reference frontal plane as a frontal vectorcardiogram.

37. The implantable medical device of claim 36, wherein the sensing means further comprises:

means for deriving a gain factor that compensates for the angular deviation of the internal lead vector out of coplanar relation with the at least one of the reference sagittal, horizontal, and frontal planes of the body that the at least one of the sagittal vectorcardiogram; horizontal vectorcardiogram, and frontal vectorcardiogram is traced into; and means for amplifying the sensed PQRST electrogram by the derived gain factor.

38. The implantable medical device of claim 35, wherein the sensing means further comprises:

means for deriving a gain factor that compensates for the angular deviation of the internal lead vector out of coplanar relation with the at least one of the reference sagittal, horizontal, and frontal planes of the body that the xyz-vectorcardiogram is related to; and means for amplifying the sensed PQRST electrogram by the derived gain factor.

39. The implantable medical device of claim 35, wherein the electrodes of the pair of electrodes are adapted to be implanted in selected locations within the right ventricle, the right atrium and the coronary sinus of the heart.

40. The implantable medical device of claim 35, wherein a first electrode of the pair of electrodes is adapted to be implanted within one of the right ventricle, the right atrium and the coronary sinus of the heart and a second electrode of me pair of electrodes is adapted to be implanted subcutaneously and remote from the heart.

41. A system for developing an xyz-vector vectorcardiogram of electrical signals of the heart accompanying depolarization and re-polarization of the muscle cells of the heart during a PQRST cardiac cycle employing an implantable medical device comprising:

an atrial electrode implanted in relation to the one of the right atrium and left atrium;

a right ventricular electrode implanted in relation to the right ventricle;

a left ventricular electrode implanted in relation to the left ventricle;

first sensing means selectively coupled to the atrial electrode and the right ventricular electrode for sensing the electrical signals of the heart along a first internal lead vector and providing a first vector signal;

second sensing means selectively coupled to the atrial electrode and the left ventricular electrode for sensing the electrical signals of the heart along a second internal lead vector and providing a second vector signal;

third sensing means selectively coupled to the left ventricular electrode and the right ventricular electrode for sensing the electrical signals of the heart along a third internal lead vector and providing a third vector signal;

means for developing an xyz-vector of a vectorcardiogram that is related to reference sagittal, horizontal, and frontal planes of the body from one or more of the first, second and third internal lead vector signals; and means for deriving the orientation and magnitude of a wave front of at least one of the P-wave, QRS wave and T-wave of the sensed PQRST electrogram over the time of occurrence of a sensed PQRST electrogram as at least one of an x-axis vector protected into the reference sagittal plane as a sagittal vectorcardiogram a y-axis vector protected into the reference horizontal plane as a horizontal vectorcardiogram, and a z-axis vector projected into the reference frontal plane as a frontal vectorcardiogram.

42. The system of claim 41, wherein:

the first sensing means further comprises:
means for deriving a first gain factor that compensates for the angular deviation of the first internal lead vector out of coplanar relation with the at least one of the reference sagittal, horizontal, and frontal planes of the body that the xyz-vectorcardiogram is related to; and
means for amplifying the sensed PQRST electrogram by the derived gain factor to provide the first vector signal;

the second sensing means further comprises:
means for deriving a second gain factor that compensates for the angular deviation of the second internal lead vector out of coplanar relation with the at least one of the reference sagittal, horizontal, and frontal planes of the body that the xyz-vectorcardiogram is related to; and
means for amplifying the sensed PQRST electrogram by the derived gain factor to provide the second vector signal; and the third sensing means further comprises:
means for deriving a third gain factor that compensates for the angular deviation of the third internal lead vector out of coplanar relation with the at least one of the reference sagittal, horizontal, and frontal planes of the body that the xyz-vectorcardiogram is related to; and
means for amplifying the sensed PQRST electrogram by the derived gain factor to provide the third vector signal.

43. A method of developing an xyz-vector vectorcardiogram of electoral signals of the heart accompanying depolarization and re-polarization of the muscle cells of the heart during a PQRST cardiac cycle employing an implantable medical device comprising:

implanting an atrial electrode in relation to the one of the right atrium and left atrium;

implanting a right ventricular electrode in relation to the right ventricle;

implanting a left ventricular electrode in relation to the left ventricle;

sensing the electrical signals of the heart along a first internal lead vector between the atrial electrode and the right ventricular electrode and providing a first internal lead vector signal;

sensing the electrical signals of the heart along a second internal lead vector between the atrial electrode and the left ventricular electrode and providing a second internal lead vector signal;

sensing the electrical signals of the heart along a third internal lead vector between the left ventricular electrode and the right ventricular electrode for and providing a third internal lead vector signal;

developing an xyz-vector of a vectorcardiogram mat is related to reference sagittal, horizontal, and frontal planes of the body from one or mare of the first, second and third internal lead vector signals; and developing the orientation and magnitude of the wave front of at least one of the P-wave, QRS wave and T-wave of the sensed PQRST electrogram over the time of occurrence of the sensed PQRST electrogram as at least one of an x-axis vector projected into the reference sagittal plane as a sagittal vectorcardiogram, a y-axis vector projected into the reference horizontal plane as a horizontal vectorcardiogram, and a z-axis vector projected into the reference frontal plane as a frontal vectorcardiogram.

44. The method of claim 43, wherein:

the step of sensing and providing the first internal lead vector signal further comprises:
deriving a first gain factor that compensates for the angular deviation of the first internal lead vector out of coplanar relation with the at least one of the reference sagittal, horizontal, and frontal planes of the body that the xyz-vectorcardiogram is related to; and
amplifying the sensed PQRST electrogram by the derived gain factor to provide the first vector signal;

the step of sensing and providing the second internal lead vector signal further comprises:
deriving a second gain factor that compensates for the angular deviation of the second internal lead vector out of coplanar relation with the at least one of the reference sagittal, horizontal, and frontal planes of the body that the xyz-vectorcardiogram is related to; and
amplifying the sensed PQRST electrogram by the derived gain factor to providing the second vector signal; and the, step of sensing and providing the third internal lead vector signal further comprises:
deriving a third gain factor that compensates for the angular deviation of the third internal lead vector out of coplanar relation with the at least one of the reference sagittal, horizontal, and frontal planes of the body that the xyz-vectorcardiogram is related to; and
amplifying the sensed PQRST electrogram by the derived gain factor to provide the third vector signal.

45. A system for developing an internal $X_P$-vector, $Y_P$-vector and $Z_P$-vector electrical signals of the heart accompanying depolarization and re-polarization of the muscle cells of the heart during a cardiac cycle in an implantable medical device capable of communicating with an external medical device, the external medical device capable of developing a reference $X_E$-vector signal, a reference $Y_E$-vector signal, and a reference $Z_E$-vector signal within a set of orthogonal reference planes defined by a reference $X_E$-vector, a reference $_E$-vector, and a reference $Z_E$-vector, the system comprising:

first, second, and third electrodes implanted in relation to the heart separated apart from one another such that a first internal lead vector is defined between the first and second electrodes, a second internal lead vector is defined between the first and third electrodes, and a third internal lead vector is defined between the second and third electrodes;

first sensing means selectively coupled to the first electrode and the second electrode for sensing and amplifying the electrical signals of the heart along the first internal lead vector at a first gain and providing a first vector signal;

second sensing means selectively coupled to the first electrode and the third electrode for sensing and amplifying the electrical signals of the heart along the second internal lead vector at a second gain and providing a second vector signal;

third sensing means selectively coupled to the second electrode and the third electrode for sensing and amplifying the electrical signals of the heart along the third internal lead vector at a third gain and providing a third vector signal;

means for adjusting the first gain to normalize the first vector signal to the reference $X_E$-vector signal to provide the $X_P$-vector signal;

means for adjusting the second gain to normalize the second vector signal to the reference $Y_E$-vector signal to provide the $Y_P$-vector signal; and means for adjusting the third gain to normalize the third vector signal to the reference $Z_E$-vector signal to provide the $Z_P$-vector signal.

46. The system of claim 45, further comprising means for developing an xyz-vector within three dimensional space referenced to the set of orthogonal reference planes defined by the reference $X_E$-vector, the reference $Y_E$-vector, and the reference $Z_E$-vector from the internal $X_P$-vector, $Y_P$-vector and $Z_P$-vector signals.

* * * * *

UNITED STATES PATENT AND TRADEMARK OFFICE
CERTIFICATE OF CORRECTION

PATENT NO. : 6,766,190 B2
DATED : July 20, 2004
INVENTOR(S) : Bozidar Ferek-Petric It is certified that error appears in the above-identified patent and that said Letters Patent is hereby corrected as shown below:

Column 27,
Line 38, delete "aver the fine" and insert -- over the time --.

Column 28,
Line 44, delete "electrogram, to" and insert -- electrogram to --.
Line 54, delete "the taxis vector", and insert -- the x-axis vector --.

Column 29,
Line 19, delete "lead sector", and insert -- lead vector --.

Column 30,
Line 52, delete "is misted to;" and insert -- is related to; --.
Line 62, delete "electrode; of the" and insert -- electrode of the --.

Column 31,
Line 26, delete "head.", and insert -- heart --.

Column 32,
Line 34, delete "amplifying stop.", and insert -- amplifying step. --.
Line 43, delete "the head;" and insert -- the heart; --.
Line 44, delete "to a head", and insert -- to a heart --.

Column 33,
Line 2, delete "ORS wave", and insert -- ORS wave --.
Line 60, delete "vectors and means", and insert -- vector; and means --.

Column 34,
Line 43, delete "me pair", and insert -- the pair --.

Column 36,
Line 3, delete "mat is", and insert -- that is --.
Line 5, delete "one or more", and insert -- one or more --.

UNITED STATES PATENT AND TRADEMARK OFFICE
CERTIFICATE OF CORRECTION

PATENT NO.    : 6,766,190 B2
DATED         : July 20, 2004
INVENTOR(S)   : Bozidar Ferek-Petric It is certified that error appears in the above-identified patent and that said Letters Patent is hereby corrected as shown below:

<u>Column 36,</u>
Line 7, delete "developing", and insert -- deriving --.
Line 37, delete "to providing", and insert -- to provide --.

Signed and Sealed this

Fourth Day of January, 2005

JON W. DUDAS
*Director of the United States Patent and Trademark Office*